(12) United States Patent
Wallach et al.

(10) Patent No.: US 7,374,909 B1
(45) Date of Patent: May 20, 2008

(54) MODULATORS OF INTRACELLULAR INFLAMMATION, CELL DEATH AND CELL SURVIVAL PATHWAYS

(75) Inventors: David Wallach, Rehovot (IL); Mark Boldin, Rehovot (IL); Nikolai Malinin, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/445,223

(22) PCT Filed: Jun. 1, 1998

(86) PCT No.: PCT/IL98/00255

§ 371 (c)(1),
(2), (4) Date: Dec. 6, 1999

(87) PCT Pub. No.: WO98/55507

PCT Pub. Date: Dec. 10, 1998

(30) Foreign Application Priority Data

| Jun. 5, 1997 | (IL) | 121011 |
| Jun. 30, 1997 | (IL) | 121199 |
| Sep. 11, 1997 | (IL) | 121746 |

(51) Int. Cl.
*C12P 21/06* (2006.01)

(52) U.S. Cl. .............. 435/69.1; 435/252.3; 435/320.1; 435/325; 536/23.1; 536/23.5

(58) Field of Classification Search .............. 536/23.1, 536/23.5; 435/325, 69.1, 252.3, 320.1; 530/350
See application file for complete search history.

(56) References Cited

U.S. PATENT DOCUMENTS

| 5,578,468 A | * | 11/1996 | Pickup et al. ............. 435/91.32 |
| 5,585,479 A | * | 12/1996 | Hoke et al. ................. 536/24.5 |
| 5,840,708 A | * | 11/1998 | Weiss ........................... 514/44 |
| 6,033,855 A | * | 3/2000 | Bertin ........................... 435/6 |

OTHER PUBLICATIONS

Siyanova, et al, 1994, Accession No. I49118, GenBank, and MPSRCH search report, 2002, us-09-445-223-1.rpr, p. 2.*
Johnstone and Thorpe. Immunochemistry in Practice, 2nd Ed., 1987, Blackwell Scientific Publications, Oxford, pp. 49-50.*
Harris et al. J. of The Am Society of Nephrology 6:1125-33, 1995.*
Ahn et al. Nature Genetics 3(4):283-91, 1993.*
Cawthon et al. Genomics 9(3):446-60, 1991.*
MPSRCH search report, 2004, us-09-445-223-2.olig-11.rni, pp. 1-2.*
Crystal (1995, Science, vol. 270, pp. 404-410).*
Verma (Sep. 1997, Nature, vol. 389, pp. 239-242).*
Deonarain (1998, Expert Opin. Ther. Pat., vol. 8, pp. 53-69).*
Miller (1995, FASEB J., vol. 9, pp. 190-199).*
Shiozaki E N et al, 2002, Proceed Natl Acad Sci, USA, 99 (7): 4197-4202.*
Shaerwin-Whyatt LM et al, 2000, Cell Death and Differentiation, 7: 155-165.*
Bowie et al (Science, 1990, 257 : 1306-1310).*
Ottilie S et al, 1997, JBC, 272 (49): 30866-30872.*
Branch, AD, 1998, TIBS 23: 45-50.*
Freshney (Culture of Animal Cells, A Manual of Basic Technique, Alan R. Liss, Inc., 1983, New York, p4.*
Dermer (Bio/Technology, 1994, 12:320.*
Gura (Science, 1995, 270:575-577).*
Burgess et al. Journal of Cell Biology, 1990, 11" 2129-2138.*
Lazar et al. Molecular and Cell Biology, 1988, 8:1247-1252.*
Tao. et al. The Journal of Immunology, 1989, 143(8): 2595-2601.*
Gillies et al. Human Antibodies and Hybridomas, 1990, 1(I):47-54).*
Alberts et al. (Molecular Biology of the Cell, 3rd edition, 1994, pp. 465).*
Shantz and Pegg (Int J of Biochem and Cell Biol., 1999, vol. 31, pp. 107-122).*
McClean et al (Eur J of Cancer, 1993, vol. 29A, pp. 2243-2248).*
Fu et al (EMBO Journal, 1996, vol. 15, pp. 4392-4401).*
Hofmann et al., "The Card domain: a new apoptotic signaling motif", *TIBS Trends in Biochemical Sciences*, vol. 22, No. 5, pp. 155-156, (1997).
Inohara et al., "Rick, a novel Protein Kinase Containing a Caspase Recruitment Domain, Interacts with CLARP and Regulates CD95-mediated Apoptosis", *J. Biol. Chem.*, vol. 273, No. 20, pp. 12296-12300, (1998).
Nelson et al., "Vacuolar H= -ATPase: from mammals to yeast and back", *Experientia*, vol. 52, pp. 1101-1110, (1996).
McCarthy et al., "RIP2 Is a Novel NF-B-activating and Cell Death-inducing Kinase", *The Journal of Biomedical Chemistry*, vol. 273, No. 27, pp. 16968-16975, (1998).
Stanger et al., "RIP: A Novel Protein Containing a Death Domain that Interacts with Fas/APO-1 (CD95) in yeast and Causes Cell Death", *CELL*, vol. 81, pp. 513-523, (1995).

* cited by examiner

*Primary Examiner*—Larry R. Helms
*Assistant Examiner*—Minh-Tam Davis
(74) *Attorney, Agent, or Firm*—Browdy and Neimark, PLLC

(57) ABSTRACT

A B1 protein, its isoforms, analogs, fragments and derivatives, DNA encoding it and recombinant production are provided. The protein is useful in the modulation of intracellular inflammation, cell death and/or cell survival pathways.

12 Claims, 8 Drawing Sheets

New Kinase Sequences

A. Amino Acid sequence: boxed - kinase domain, underlined - CARD domain.

```
           10         20         30         40         50         60         70         80         90        100
           |          |          |          |          |          |          |          |          |          |
  1 MNGEAICSAL PTIPYHKLAD LRYLSRGASG TVSSARHADW RVQVAVKHLH IHTPILDSER KDVLREAEIL HKARFSYIFP IIGICNEPEF LGIVTEYMPH 100
101 GSLNELLHRK TEYPDVAWPL RFRILHEIAL GVNYLHNMTP NILLDNEFHV KIADFGLSKW RMMSLSQSPS SKSAPEGGTI IYMPPENYEP 200
201 GQKSRASIKH DIYSYAVITW EVLSRKQPFE DVTNPLQIMY SVSQGIRPVI NEESLPYDIP HRARMISLLE SGWAQNPDFR PSFLKCLIEL EPVLRTFEEI 300
301 TFLEAVIQLK KTKLQSVSSA IHLCDKKKME LSLNIPVNIG PQEESCGSSQ LHENSGSPET SRSLPAPQDN DFLSRKAQIC YFMKLHHCPG NHSWDSTISG 400
401 SQRAAFCDHK TTPCSSAIIN PLSTAGNSER LQPGLAQQMI QSKREFIVNQ MTEACLNQSL DALLSRDLIM KEDYELVSTK PTRTSKVHQL LDTTDIQGEE 500
501 FAKVIVQKLK DNKQMGLQPY PEILVVSRSP SLNLLQNKSM                                                               540
```

B. Nucleotide sequence.

```
           10         20         30         40         50         60         70         80         90        100
           |          |          |          |          |          |          |          |          |          |
   1 GGCCATTATG GATGGAATGG CGGCCTGCTG CGGCGCTACG GCGTTGGCAG CGGTGTGAGC CAGTCTCTAG AAAGAAGTC AGCTCTGTT CGGAGAAGCA GCGCTGGCG TGGGCCATCC 100
 101 GGGAATGGG CGCCCTCGTG CGGCCTCGTG CGGCCGGCAA AGGGTCTTG CCGGCCTCGC TGGTGCAGGG GCCTATCTGG GCGCTGAGC GCGCCCCTGC GCGGCGTGGG 200
 201 AGCCTTGGGA GCGGCCGCAG CGGGGCGCAC CAGGGGCCAC ACCCGAACC GGGCTCTTG CCCGGACCA TGAACGGGGA GGCCATGTGC AGCGCCCTGC CACCATTCC 300
 301 CTACCACAAA CTCGCCGACC TCGCTACCT GAGCCGTGGC AGTGAAGAA AGGATGTTT AAGAGAAGCT GAAATTTTAC ACAAAGTCA TGAACTCCTA CATAGGAAAA CTGAATATCC 500
 401 CACCTGCACA TCCACACTCC GCTGCTGAC AGTGAAGAA AGGATGTTT AAGAGAAGCT GAAATTTTAC ACAAAGTCA TGAACTCCTA CATAGGAAAA CTGAATATCC 500
 501 TTTTGGGAAT TTGCAATGA CCTGCATTGA GATTTCGCAT TACTCAATAC ATGCCAAATG GATCATTAAA TGAACTCCTA CATAGGAAAA CTGAATATCC 600
 601 TGATGTTGCT TGGCATTGA GATTTCGCAT TACTCAATAC ATGCCAAATG GATCATTAAA CCTGCACAAT ATGACTCCTC CTTTACTTCA TCATGACTTG 700
 701 AAGACTCAGA ATATCTTATT GGACAATGAA TTTCATCTTA AGAATGCAGA TTTTGGTTTA TCAAAGTGGC GCAAAGTGGC ATAATGTATA TCAAAGTGGC CCTCGTCACAG TCACGAAGTA 800
 801 GCAAATCTGC ACCAGAAGGA GGGACAATTA TTTATATGCC ACCTGAAAAC CCTTTGAAG TGTGACCTG GACAAAATC AAGGGCCAGT ATAAGCACG TCACGAAGTA 900
 901 CTATGCAGTT ATCACAATGG AAGTGTTATC CAGAAAACAG CCTTTGAAG ATGTCACCAA TCCTTTGCAG ATAATGTATA GTGTGTCACA AGGACATCGA 1000
1001 CCTGTTATTA ATGAAGAAAG TTTGCCATAT GATATACCTC CAGCACCGGAC CAGTCTCTAG TATGATCTCT CTAATAGAAG GTGAGCACCAG CGGCTATCTGG ACABAAGAAT CA AAATCCA GATGAAAGAC 1100
1101 CATCTTTCTT AAAATGTTTA ATAGAACTTG AACCAGTTG CCGAGCACG GAAGAATAA CTTTTCTTGA CATACCTGTA AGTCTGTATT CACCTAAAGA AAACAAAGTT 1200
1201 ACAGAGTGTT TCAAGTGCCA TTCACCATG TGACAAGAAG AAATGGAAT TATCTCTGAA CATACCTGTA AATCATGGTC CAC AAGAGGA ATCATGTGGA 1300
1301 TCCTCTCAGC TCCATGAAAA TAGTGGTTCT CCTGAAACTT CAAGCTCCT GCCAGTCTGT CAAGACAAATG ATTTTTAATC TAC AAAAGCT CAAGACTGTT 1400
1401 ATTTTATGAA GCTGCATCAC TGTCCTGGAA ATCACAGTTG GGATAGCACC AATTTCTGGAT CTCAAAGTGT GACATCTGT GAT CACAAGA CCACTCCATG 1500
1501 CTCTTCAGCA ATAATAAATC TGCAGGAAAC TGCAGGAAAT GCCCCTTCT TGCAGCCTGG TATAGCCCAG CAGTGGATCC AGAGCGACCA AGGGCAAAAG GGAAGACATT 1600
1601 GTGAACCAAA TGACAGAAGC CTGCCTTAAC CAGTCGCTAG ATGCCCTTCT GTCCAGGGAC TTGATCATGA AAGAGGACTA TGAACTTGTT AGTACCAAGC 1700
1701 CTACAAGGAC CTCAAAGTC AGACAATTAC TAGACACTAC TGACATCCAA GGAAGAATT TGCCAAAGT TATAGTACAA AAATGAAAG ATAACAAACA 1800
1801 AATGGGTCTT CAGCCTTACC CGGAAATACT TGTGGTTTCT AGATACCAT CTTTAATTT ACTTCAAAAT AAAAGCATGT AATGACTGT TTTTCAAGAA 1900
1901 GAAATGTGTT TCATAAAGG ATATTTATAT CTCTGTTGCT TTGACTTTT TTATATAAAA TCCGTGAGTA TTAAAGCTW AAWHAANGKT CTTSRKTAA 2000
2001 ATATTAGTCT CCCTCCAGTA CACTCGACGA TTTTTTAA TTANTACAAG TAAAAGTTG AATTTGAAAA AAAAAAAA AAAAAAAA 2098
```

Fig. 3

Deletion analysis of B1 ability to activate NF-kB transcriptional factor

Fig. 6

SEQUENCE LISTING

```
<160> NUMBER OF SEQ ID NOS: 5

<210> SEQ ID NO 1
<211> LENGTH: 540
<212> TYPE: PRT
<213> ORGANISM: Homo sapiens

<400> SEQUENCE: 1

Met Asn Gly Glu Ala Ile Cys Ser Ala Leu Pro Thr Ile Pro Tyr His
1               5                   10                  15

Lys Leu Ala Asp Leu Arg Tyr Leu Ser Arg Gly Ala Ser Gly Thr Val
            20                  25                  30

Ser Ser Ala Arg His Ala Asp Trp Arg Val Gln Val Ala Val Lys His
        35                  40                  45

Leu His Ile His Thr Pro Leu Leu Asp Ser Glu Arg Lys Asp Val Leu
    50                  55                  60
```

```
Arg Glu Ala Glu Ile Leu His Lys Ala Arg Phe Ser Tyr Ile Phe Pro
 65                  70                  75                  80

Ile Leu Gly Ile Cys Asn Glu Pro Glu Phe Leu Gly Ile Val Thr Glu
                 85                  90                  95

Tyr Met Pro Asn Gly Ser Leu Asn Glu Leu Leu His Arg Lys Thr Glu
            100                 105                 110

Tyr Pro Asp Val Ala Trp Pro Leu Arg Phe Arg Ile Leu His Glu Ile
        115                 120                 125

Ala Leu Gly Val Asn Tyr Leu His Asn Met Thr Pro Pro Leu Leu His
    130                 135                 140

His Asp Leu Lys Thr Gln Asn Ile Leu Leu Asp Asn Glu Phe His Val
145                 150                 155                 160

Lys Ile Ala Asp Phe Gly Leu Ser Lys Trp Arg Met Met Ser Leu Ser
                165                 170                 175

Gln Ser Arg Ser Ser Lys Ser Ala Pro Glu Gly Gly Thr Ile Ile Tyr
            180                 185                 190

Met Pro Pro Glu Asn Tyr Glu Pro Gly Gln Lys Ser Arg Ala Ser Ile
        195                 200                 205

Lys His Asp Ile Tyr Ser Tyr Ala Val Ile Thr Trp Glu Val Leu Ser
    210                 215                 220

Arg Lys Gln Pro Phe Glu Asp Val Thr Asn Pro Leu Gln Ile Met Tyr
225                 230                 235                 240

Ser Val Ser Gln Gly His Arg Pro Val Ile Asn Glu Glu Ser Leu Pro
                245                 250                 255

Tyr Asp Ile Pro His Arg Ala Arg Met Ile Ser Leu Ile Glu Ser Gly
            260                 265                 270

Trp Ala Gln Asn Pro Asp Glu Arg Pro Ser Phe Leu Lys Cys Leu Ile
        275                 280                 285

Glu Leu Glu Pro Val Leu Arg Thr Phe Glu Glu Ile Thr Phe Leu Glu
    290                 295                 300

Ala Val Ile Gln Leu Lys Lys Thr Lys Leu Gln Ser Val Ser Ser Ala
305                 310                 315                 320

Ile His Leu Cys Asp Lys Lys Met Glu Leu Ser Leu Asn Ile Pro
                325                 330                 335

Val Asn His Gly Pro Gln Glu Glu Ser Cys Gly Ser Ser Gln Leu His
            340                 345                 350

Glu Asn Ser Gly Ser Pro Glu Thr Ser Arg Ser Leu Pro Ala Pro Gln
        355                 360                 365

Asp Asn Asp Phe Leu Ser Arg Lys Ala Gln Asp Cys Tyr Phe Met Lys
    370                 375                 380

Leu His His Cys Pro Gly Asn His Ser Trp Asp Ser Thr Ile Ser Gly
385                 390                 395                 400

Ser Gln Arg Ala Ala Phe Cys Asp His Lys Thr Thr Pro Cys Ser Ser
                405                 410                 415

Ala Ile Ile Asn Pro Leu Ser Thr Ala Gly Asn Ser Glu Arg Leu Gln
            420                 425                 430

Pro Gly Ile Ala Gln Gln Trp Ile Gln Ser Lys Arg Glu Asp Ile Val
        435                 440                 445

Asn Gln Met Thr Glu Ala Cys Leu Asn Gln Ser Leu Asp Ala Leu Leu
    450                 455                 460

Ser Arg Asp Leu Ile Met Lys Glu Asp Tyr Glu Leu Val Ser Thr Lys
465                 470                 475                 480
```

```
Pro Thr Arg Thr Ser Lys Val Arg Gln Leu Leu Asp Thr Thr Asp Ile
                485                 490                 495

Gln Gly Glu Glu Phe Ala Lys Val Ile Val Gln Lys Leu Lys Asp Asn
            500                 505                 510

Lys Gln Met Gly Leu Gln Pro Tyr Pro Glu Ile Leu Val Val Ser Arg
        515                 520                 525

Ser Pro Ser Leu Asn Leu Leu Gln Asn Lys Ser Met
    530                 535                 540

<210> SEQ ID NO 2
<211> LENGTH: 2098
<212> TYPE: DNA
<213> ORGANISM: Homo sapiens

<400> SEQUENCE: 2
ggccattatg gatggatggg cggcgctacg gcgttggcac cagtctctag aaaagaagtc      60
agctctggtt cggagaagca gcggctggcg tgggccatcc ggggaatggg cgccctcgtg     120
acctagtgtt gcggggcaaa aagggtcttg ccggcctcgc tcgtgcaggg gcgtatctgg     180
gcgcctgagc gcggcgtggg agccttggga gccgccgcag caggggcac  acccggaacc     240 ggcctgagcg cccgggacca tgaacgggga ggccatctgc agcgccctgc ccaccattcc     300
ctaccacaaa ctcgccgacc tgcgctacct gagccgcggc gcctctggca ctgtgtcgtc     360
cgcccgccac gcagactggc gcgtccaggt ggccgtgaag cacctgcaca tccacactcc     420
gctgctcgac agtgaaagaa aggatgtttt aagagaagct gaaattttac acaaagctag     480
atttagttac attttttccaa ttttgggaat ttgcaatgag cctgaatttt tgggaatagt     540
tactgaatac atgccaaatg gatcattaaa tgaactccta cataggaaaa ctgaatatcc     600
tgatgttgct tggccattga gatttcgcat cctgcatgaa attgcccttg gtgtaaatta     660
cctgcacaat atgactcctc ctttacttca tcatgacttg aagactcaga atatcttatt     720
ggacaatgaa tttcatgtta agattgcaga ttttggttta tcaaagtggc gcatgatgtc     780
cctctcacag tcacgaagta gcaaatctgc accagaagga gggacaatta tttatatgcc     840
acctgaaaac tatgaacctg acaaaaaatc aagggccagt atcaagcacg atatatatag     900
ctatgcagtt atcacatggg aagtgttatc cagaaaacag ccttttgaag atgtcaccaa     960 tccttttgcag ataatgtata gtgtgtcaca aggacatcga cctgttatta tgaagaaag    1020 tttgccatat gatataccct accgagcacg tatgatctct ctaatagaaa gtggatgggc    1080
acaaaatcca gatgaaagac catctttctt aaaatgtttta atagaacttg aaccagtttt    1140
gagaacattt gaagagataa cttttcttga agctgttatt cagctaaaga aaacaaagtt    1200
acagagtgtt tcaagtgcca ttcacctatg tgacaagaag aaaatggaat tatctctgaa    1260
catacctgta aatcatggtc cacaagagga atcatgtgga tcctctcagc tccatgaaaa    1320
tagtggttct cctgaaactt caaggtccct gccagctcct caagacaatg ttttttatc    1380 tagaaaagct caagactgtt atttttatgaa gctgcatcac tgtcctggaa atcacagttg    1440
ggatagcacc atttctggat ctcaaagggc tgcattctgt gatcacaaga ccactccatg    1500
ctcttcagca ataataaatc cactctcaac tgcaggaaac tcagaacgtc tgcagcctgg    1560
tatagcccag cagtggatcc agagcaaaag ggaagacatt gtgaaccaaa tgacagaagc    1620
ctgccttaac cagtcgctag atgcccttct gtccagggac ttgatcatga agaggacta    1680 tgaacttgtt agtaccaagc ctacaaggac ctcaaaagtc agacaattac tagacactac    1740
tgacatccaa ggagaagaat ttgccaaagt tatagtacaa aaattgaaag ataacaaaca    1800
```

-continued

```
aatgggtctt cagccttacc cggaaatact tgtggtttct agatcaccat ctttaaattt    1860
acttcaaaat aaaagcatgt aagtgactgt ttttcaagaa gaaatgtgtt tcataaaagg    1920
atatttatat ctctgttgct ttgactttt ttatataaaa tccgtgagta ttaaagcttw    1980
awwraargkt ctttsrktaa atattagtct ccctccatga cactgcagta ttttttttaa   2040
ttaatacaag taaaaagttg aatttgaaaa aaaaaaaaaa aaaaaaaaaa aaaaaaaa     2098

<210> SEQ ID NO 3
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Residue at postion 1 is modified by an acetyl
      group.
<220> FEATURE:
<221> NAME/KEY: misc_feature
<222> LOCATION: (4)..(4)
<223> OTHER INFORMATION: Residue at postion 4 is modified by
      a-(4-methyl-coumaryl-7-amide).
<220> FEATURE:
<221> NAME/KEY: misc_feature
<222> LOCATION: (4)..(4)
<223> OTHER INFORMATION: Residue at postion 4 is modified by an
      AC-DEVD-AMC group.

<400> SEQUENCE: 3

Asp Glu Val Asp
1

<210> SEQ ID NO 4
<211> LENGTH: 30
<212> TYPE: DNA
<213> ORGANISM: Artificial
<220> FEATURE:
<223> OTHER INFORMATION: synthetic

<400> SEQUENCE: 4
cagaattcca gagtgtttca agtgccattc                                       30

<210> SEQ ID NO 5
<211> LENGTH: 30
<212> TYPE: DNA
<213> ORGANISM: Artificial
<220> FEATURE:
<223> OTHER INFORMATION: synthetic

<400> SEQUENCE: 5
aactcgagac ttacatgctt ttattttgaa                                       30
```

MODULATORS OF INTRACELLULAR INFLAMMATION, CELL DEATH AND CELL SURVIVAL PATHWAYS

The present application is a 371 National Stage application of PCT/IL98/00255, filed Jun. 1, 1998, which claims foreign priority from IL121746, filed Sep. 11, 1997, IL121199, filed Jun. 20, 1997, and IL121011, filed Jun. 5, 1997. The entire contents of prior application PCT/IL98/00255 are herein incorporated by reference.

FIELD OF THE INVENTION

The present invention is generally in the field of modulators of intracellular cell death and cell survival pathways mediated by, amongst others, the receptors of the TNF/NGF superfamily of receptors and their associated intracellular adaptor proteins, and caspase and kinase enzymes. More specifically, the present invention concerns a new protein, originally designated CBK, but now designated B1, its isoforms, analogs, fragments and derivatives, which appears to be capable of interacting, directly or indirectly, with various intracellular proteins and enzymes that belong to the cell death, cell survival and inflammation pathways, and hence, which is a modulator of these pathways.

BACKGROUND OF THE INVENTION

The Tumor Necrosis Factor/Nerve Growth Factor (TNF/NGF) receptor superfamily is defined by structural homology between the extracellular domains of its members (Bazan, 1993; Beutler and van Huffel, 994; Smith et al., 1994). Except for two receptors, the p55 TNF receptor and Fas/APO1, the various members of this receptor family do not exhibit clear similarity of structure in their intracellular domains. Nevertheless, there is much similarity of function between the receptors, indicating that they share common signaling pathways. One example for this similarity is the ability of several receptors of the TNF/NGF family to activate the transcription factor NF-κB. This common ability was ascribed to a capability of a cytoplasmic protein that activates NF-κB, TNF Receptor Associated Factor 2 (TRAF2) to bind to the structurally-dissimilar intracellular domains of several of the receptors of the TNF/NGF family. By what mechanisms TRAF2 acts and how its responsiveness to the different receptors to which it binds is coordinated, is not known.

TRAF2 is a member of a recently described family of proteins called TRAF that includes several proteins identified as, for example, TRAF1, TRAF2 (Rothe, M., Wong, s.c., Henzel, W. J. and Goeddel, D (1994) Cell 78:681-692; PCT published application WO 95/33051), TRAF3 (Cheng, G. et al. (1995)), and TRAF6 (see Cao et al., 1996a).

All proteins belonging to the TRAF family share high degree of amino acid identity in their C-terminal domains, while their N-terminal domains may be unrelated. As shown in a schematic illustration of TRAF2 (FIG. 1), the molecule contains a ring finger motif and two TFIIIA-like zinc finger motifs at its C-terminal area. The C-terminal half of the molecule includes a region known as the "TRAF domain" containing a potential leucine zipper region extending between amino acids 264-358 (called N-TRAF), and another part towards the carboxy end of the domain between amino acids 359-501 (called C-TRAF) which is responsible for TRAF binding to the receptors and to other TRAF molecules to form homo- or heterodimers.

Activation of the transcription factor NF-κB is one manifestation of the signaling cascade initiated by some of the TNF/NGF receptors and mediated by TRAF2. NF-κB comprises members of a family of dimer-forming proteins with homology to the Rel oncogene which, in their dimeric form, act as transcription factors. These factors are ubiquitous and participate in regulation of the expression of multiple genes. Although initially identified as a factor that is constitutively present in B cells at the stage of IgK light chain expression, NF-κB is known primarily for its action as an inducible transcriptional activator. In most known cases NF-κB behaves as a primary factor, namely the induction of its activity is by activation of pre-existing molecules present in the cell in their inactive form, rather than its de-novo synthesis which in turn relies on inducible transcription factors that turn-on the NF-κB gene. The effects of NF-κB are highly pleiotropic. Most of these numerous effects share the common features of being quickly induced in response to an extracellular stimulus. The majority of the NF-κB-activating agents are inducers of immune defense, including components of viruses and bacteria, cytokines that regulate immune response, UV light and others. Accordingly, many of the genes regulated by NF-κB contribute to immune defense (see Blank et al., 1992; Grilli et al., 1993; Baeuerle and Henkel, 1994, for reviews).

One major feature of NF-κB-regulation is that this factor can exist in a cytoplasmic non-DNA binding form which can be induced to translocate to the nucleus, bind DNA and activate transcription. This dual form of the NF-κB proteins is regulated by I-κB—a family of proteins that contain repeats of a domain that has initially been discerned in the erythrocyte protein ankyrin (Gilmore and Morin, 1993). In the unstimulated form, the NF-κB dimer occurs in association with an I-κB molecule which imposes on it cytoplasmic location and prevents its interaction with the NF-κB-binding DNA sequence and activation of transcription. The dissociation of I-κB from the NF-κB dimer constitutes the critical step of its activation by many of its inducing agents (DiDonato et al., 1995). Knowledge of the mechanisms that are involved in this regulation is still limited. There is also just little understanding of the way in which cell specificity in terms of responsiveness to the various NF-κB-inducing agents is determined.

One of the most potent inducing agents of NF-κB is the cytokine tumor necrosis factor (TNF). There are two different TNF receptors, the p55 and p75 receptors (p55-R and p75-R). Their expression levels vary independently among different cells (Vandenabeele et al., 1995). The p75 receptor responds preferentially to the cell-bound form of TNF (TNF is expressed both as a beta-transmembrane protein and as a soluble protein) while the p55 receptor responds just as effectively to soluble TNF molecules (Grell et al., 1995). The intracellular domains of the two receptors are structurally unrelated and bind different cytoplasmic proteins. Nevertheless, at least part of the effects of TNF, including the cytocidal effect of TNF and the induction of NF-κB, can be induced by both receptors. This feature is cell specific. The p55 receptor is capable of inducing a cytocidal effect or activation of NF-κB in all cells that exhibit such effects in response to TNF. The p75-R can have such effects only in some cells. Others, although expressing the p75-R at high levels, show induction of the effects only in response to stimulation of the p55-R (Vandenabeele et al., 1995). Apart from the TNF receptors, various other receptors of the TNF/NGF receptor family: CD30 (McDonald et al., 1995), CD40 (Berberich et al., 1994; Lalmanach-Girard et al., 1993), the lymphotoxin beta receptor and, in a few types of cells, Fas/APO1 (Rensing-Ehl et al., 1995), are also capable of inducing activation of NF-κB. The IL-1 type I receptor, also effectively triggering NF-κB activation, shares most of the effects of the TNF receptors despite the fact that it has no structural similarity to them.

The activation of NF-κB upon triggering of these various receptors results from induced phosphorylation of its associated I-κB molecules. This phosphorylation tags I-κB to degradation, which most likely occurs in the proteasome. The nature of the kinase that phosphorylates I-κB, and its mechanism of activation upon receptor triggering is still unknown. However, in the recent two years some knowledge has been gained as to the identity of three receptor-associated proteins that appear to take part in initiation of the phosphorylation (see diagrammatic illustration in FIGS. 2a and 6). A protein called TRAF2, initially cloned by D. Goeddel and his colleagues (Rothe et al., 1994), seems to play a central role in NF-κB-activation by the various receptors of the TNF/NGF family. The protein, which when expressed at high levels can by itself trigger NF-κB activation, binds to activated p75 TNF-R (Rothe et al., 1994), lymphotoxin beta receptor (Mosialos et al., 1995), CD40 (Rothe et al., 1995a) and CD-30 (unpublished data) and mediates the induction of NF-κB by them. TRAF2 does not bind to the p55 TNF receptor nor to Fas/APO1, however, it can bind to a p55 receptor-associated protein called TRADD and TRADD has the ability to bind to a Fas/APO1-associated protein called MORT1 (or FADD—see Boldin et al. 1995b and 1996). Another receptor-interacting protein, called RIP (see Stanger et al., 1995) is also capable of interacting with TRAF2 as well as with FAS/APO1, TRADD, the p55 TNF receptor and MORT-1. Thus, while RIP has been associated with cell cytotoxicity induction (cell death), its ability to interact with TRAF2 also implicates it in NF-κB activation and it also may serve in addition to augment the interaction between FAS/APO1, MORT-1, p55 TNF receptor and TRADD with TRAF2 in the pathway leading to NF-κB activation. These associations apparently allow the p55 TNF receptor and Fas/APO1 to trigger NF-κB activation (Hsu et al., 1995; Boldin et al., 1995; Chinnaiyan et al., 1995; Varfolomeev et al., 1996; Hsu et al., 1996). The triggering of NF-κB activation by the IL-1 receptor occurs independently of TRAF2 and may involve a recently-cloned IL-1 receptor-associated protein-kinase called IRAK (Croston et al., 1995).

By what mechanism TRAF2 acts is not clear. Several cytoplasmic molecules that bind to TRAF2 have been identified (Rothe et al., 1994; Rothe et al., 1995b). However, the information on these molecules does not provide any clue as to the way by which TRAF2, which by itself does not possess any enzymatic activity, triggers the phosphorylation of I-κB. There is also no information yet of mechanisms that dictate cell-specific pattern of activation of TRAF2 by different receptors, such as observed for the induction of NF-κB by the two TNF receptors.

In addition to the above mentioned, of the various TRAF proteins, it should also be noted that TRAF2 binds to the p55 (CD120a) and p75 (CD120b) TNF receptors, as well as to several other receptors of the TNF/NGF receptor family, either directly or indirectly via other adaptor proteins as noted above, for example with reference to the FAS/APO1 receptor, and the adaptor proteins MORT-1, TRADD and RIP. As such, TRAF2 is crucial for the activation of NF-κB (see also Wallach, 1996). However, TRAF3 actually inhibits activation of NF-κB by some receptors of the TNF/NGF family (see Rothe et al., 1995a), whilst TRAF6 is required for induction of NF-κB by IL-1 (see Cao et al., 1996a).

Accordingly, as regards NF-κB activation and its importance in maintaining cell viability, the various intracellular pathways involved in this activation have heretofore not been clearly elucidated, for example, how the various TRAF proteins, are involved directly or indirectly.

Furthermore, as is now known regarding various members of the TNF/NGF receptor family and their associated intracellular signaling pathways inclusive of various adaptor, mediator/modulator proteins (see brief reviews and references in, for example, co-pending co-owned Israel Patent Application Nos. 114615, 114986, 115319, 116588), TNF and the FAS/APO1 ligand, for example, can have both beneficial and deleterious effects on cells. TNF, for example, contributes to the defense of the organism against tumors and infectious agents and contributes to recovery from injury by inducing the killing of tumor cells and virus-infected cells, augmenting antibacterial activities of granulocytes, and thus in these cases the TNF-induced cell killing is desirable. However, excess TNF can be deleterious and as such TNF is known to play a major pathogenic role in a number of diseases such as septic shock, anorexia, rheumatic diseases, inflammation and graft-vs-host reactions. In such cases TNF-induced cell killing is not desirable. The FAS/APO1 ligand, for example, also has desirable and deleterious effects. This FAS/APO1 ligand induces via its receptor the killing of autoreactive T cells during maturation of T cells, i.e. the killing of T cells which recognize self-antigens, during their development and thereby preventing autoimmune diseases. Further, various malignant cells and HIV-infected cells carry the FAS/APO1 receptor on their surface and can thus be destroyed by activation of this receptor by its ligand or by antibodies specific thereto, and thereby activation of cell death (apoptosis) intracellular pathways mediated by this receptor. However, the FAS/APO1 receptor may mediate deleterious effects, for example, uncontrolled killing of tissue which is observed in certain diseases such as acute hepatitis that is accompanied by the destruction of liver cells.

In view of the above, namely, that receptors of the TNF/NGF family can induce cell death pathways on the one hand and can induce cell survival pathways (via NF-κB induction) on the other hand, there apparently exists a fine balance, intracellularly between these two opposing pathways. For example, when it is desired to achieve maximal destruction of cancer cells or other infected or diseased cells, it would be desired to have TNF and/or the FAS/APO1 ligand inducing only the cell death pathway without inducing NF-κB. Conversely, when it is desired to protect cells such as in, for example, inflammation, graft-vs-host reactions, acute hepatitis, it would be desirable to block the cell killing induction of TNF and/or FAS/APO1 ligand and enhance, instead, their induction of NF-κB. Likewise, in certain pathological circumstances it would be desirable to block the intracellular signaling pathways mediated by the p75 TNF receptor and the IL-1 receptor, while in others it would be desirable to enhance these intracellular pathways.

Recently, the present inventors have isolated a kinase called NIK (Israel Patent Application Nos. 117800, 119133 and WO 97/37016) which is capable of binding to TRAF2 and is directly involved in the phosphorylation reactions leading to induction of NF-κB activation.

In addition, a number of caspases have recently been isolated by a number of researchers (including the present inventors (see co-pending, co-owned Israel Patent Application No. IL 120759)), which interact with the above noted adaptor proteins (e.g. MORT-1/FADD) or with complexes between the adaptor proteins and the various receptors of the TNF/NGF receptor family and which effect the proteolytic reactions leading to apoptotic cell death. Thus, direct modulation of these caspases would be desired in the situations noted above when it is desired to inhibit or enhance cell death, for example, when it is desired to inhibit cell death it would be desirable to inhibit the activity of these caspases. In this respect it has been reported (see review in Hofmann et al., 1997) that there exists a region called a prodomain in many of these caspases that is also present in a number of adaptor proteins such as, for example, RAIDD (which interacts with RIP, TRADD and thereby with MORT-1/FADD, the p55-TNF-R and FAS/APO1), an adaptor protein of the cell death pathway; and c-IAP1, c-IAP2, two proteins which appear to be inhibitors of apoptosis and which themselves interact with TRAF2, and thereby may be inhibitors of caspases or may otherwise stimulate TRAF2 involvement in the cell survival pathway resulting in induction of NF-κB activation. As such this prodomain has also been designated as CARD for 'caspase recruitment domain' (see Hofmann et al., 1997). This prodomain (CARD) therefore represents another target for modulation of the intracellular signaling pathways associated with cell death induction.

Moreover, recently there has been described (see Review by Yang and Korsmeyer, 1996) another family of proteins, called the BCL2 protein family, of which the proteins BCL2, its homolog BCL-X including the two forms thereof being BCL-$X_L$ and the alternatively spliced BCL-$X_S$, MCL1, A1, BAK, BAD, BAG1, BAX, the adenovirus E1B-19k, and the *Caenorhabditis elegans* (*C. elegans*) CED-9 protein are all members. Of these proteins it has been observed that BCL2, BCL-$X_L$, E1B-19k and CED-9 function to inhibit apoptosis, or to protect against apoptosis induced by various intracellular signaling pathways (see Yang and Korsmeyer, 1996). BCL2 and BCL-$X_L$ are also apparently intracellular membrane-bound proteins localized to mitochondria, as well as smooth endoplasmic reticulum, and the perinuclear membrane, the C-terminus of these proteins having a signal anchor sequence responsible for targeting and insertion thereof into the outer mitochondrial membrane and the other, above noted, intracellular membranes. Once anchored in the various intracellular membranes the BCL2 and BCL-$X_L$ proteins are exposed to the cytosol where they can interact with various other intracellular proteins.

How BCL2, BCL-$X_L$, E1B-19k and CED-9 protect cells has not yet been fully elucidated, but it appears that their effect is apparently upstream of the cell death effectors being the various caspases noted above, such as, for example ICE and ICE-like proteases of the ICE/CED-3 family including CPP32/Yama, ICE-LAP3 (Mch3), ICH-1 and others. In fact, CED-9 was found to be a specific inhibitor of the *C.elegans* death effector proteases CED-3 and CED-4, and BCL2 is apparently an inhibitor of ICH-1 (also called NEDD2), in particular, the ICH-$I_L$ form which promotes cell death. Thus, while the precise mechanism of inhibition of apoptosis by BCL2, BCL-$X_L$, CED-9 and E1B-19k, is not clear, it is apparently upstream of the ICE-CED-3 proteases which are the death effectors (see review of Yang and Korsmeyer, 1996, as well as Chinnaiyan et al., 1996).

As regards the other BCL2 family members noted above, BAX is a cell death promoter. BAX binds to itself and in the form of such BAX homodimers it promotes apoptosis. BAX also binds to BCL2 and BCL-$X_L$ and such heterodimers are associated with BCL2's protective effect against apoptosis. Thus the balance between the amounts of BAX/BAX homodimers and BAX/BLC2 heterodimers determines whether cells will be susceptible to apoptosis or whether they will be protected against apoptosis. BAX is also apparently an intracellular membrane-bound protein also being localized to a large degree to the outer mitochondrial membrane (for above mentioned concerning BAX, see also review by Yang and Korsmeyer, 1996). Further, the above noted BAK and BAD proteins also act as negative regulators of BCL2 and BCL-$X_L$ activity, namely, they repress the ability of BCL2 and BCL-$X_L$ to protect cells from apoptosis. It appears that both BAK and BAD bind BCL2 and BCL-$X_L$ and thereby prevent BAX from binding to BCL2 and BCL-$X_L$ resulting in increased amounts of BAX/BAX homodimers and subsequently increased cell death (see review by Yang and Korsmeyer, 1996). In this regard it also appears that BAK functions to block the death-repressor activity of BCL2 and BCL-$X_L$ directly as BAK/BCL2 and BAK/BCL-$X_L$ heterodimers lack the ability to protect cells from apoptosis. BAD appears to act more like a competitive inhibitor for BAX binding to BCL2 and BCL-$X_L$, as BAD may replace BAX from BAX/BCL2 and BAX/BCL-$X_L$ heterodimers, thereby providing for increased amounts of death-promoting BAX/BAX homodimers. While BAK also appears to be an intracellular membrane bound protein localized to, amongst others, mitochondrial outer membranes, BAD, however, is apparently devoid of a membrane anchor sequence and as such is not a membrane-bound protein (see review by Yang and Korsmeyer, 1996).

Another of the above members of the BCL2 family is BAG1 (see Yang and Korsmeyer, 1996) which is a positive modulator of BCL2 activity leading to enhanced BCL2 protective activity against apoptosis and even providing for BCL2 protective activity against apoptosis in cells induced to undergo apoptosis by signals not usually suppressed by BCL2.

It should also be noted that the above mentioned alternatively spliced form of BCL-$X_L$, namely the BCL-$X_S$ protein is also an antagonist of BCL-$X_L$ and BCL2 activity, and blocks their protective activity against apoptosis (see also review of Yang and Korsmeyer, 1996).

In view of the above mentioned it appears that the BCL2 family of proteins play a role in regulating cell death or cell survival pathways intracellularly and a shift in the balance from proteins of this family that actively block apoptosis to those that promote apoptosis or inhibit anti-apoptotic activity may result in increased cell death, and likewise, a shift in the balance the other way may result in increased cell survival.

Accordingly, when it is desired to increase cell death by increasing apoptosis in cells under the circumstances noted above, it would be desirable to block the activity of BCL2, BCL-$X_L$ and other members of this family which suppress or inhibit apoptosis, or to increase the activity of BAX, BAK, BAD, BCL-$X_S$ and other members of this family which promote apoptosis or inhibit anti-apoptotic activities of BCL2 or BCL-$X_L$. Likewise, when it is desired to increase cell survival in cells by decreasing apoptosis, it would be desirable to increase the activity of BCL2, BCL-$X_L$ and other members of this family which suppress or inhibit apoptosis, or to decrease the activity of apoptosis promoters of this family as noted above.

It is an object of the present invention to provide novel proteins, including isoforms, analogs, fragments or derivatives thereof which are capable of modulating the intracellular signaling pathways leading to inflammation, cell death or cell survival, this modulation being possibly via the prodomain (CARD) of the various caspases or via kinase domains of the various kinases involved in NF-κB activation. Such novel proteins of the invention would therefore possibly be direct modulators of caspase activity (cell death pathway) and/or NF-κB activation via kinase activity (cell survival pathway). Likewise, the novel proteins of the invention are possibly indirect modulators of the intracellular biological activity of a variety of other proteins involved in the inflammation, cell death or survival pathways (e.g. FAS/APO1, p55 TNF-R, p75 TNF-R, IL-1-R, MORT-1, TRADD, RIP, TRAF2, NIK, and others). Likewise, this modulation may also possibly be by direct or indirect interaction with members of the BCL2 family of proteins, the novel proteins of the present invention may be able to modulate the activity of BCL2 or other proteins of this family and in this sense the novel proteins of the invention may be indirect modulators of the various caspases, which, in turn, are modulated by members of the BCL2 family of proteins.

Another object of the invention is to provide antagonists (e.g. antibodies, peptides, organic compounds, or even some isoforms) to the above novel proteins, including isoforms, analogs, fragments and derivatives thereof, which may be used to inhibit the inflammation, cell death or survival signaling processes, when desired.

A further object of the invention is to use the above novel proteins, isoforms, analogs, fragments and derivatives thereof, to isolate and characterize additional proteins or factors, which may be involved in regulation of the inflammation, cell death or survival pathways and influence their activity, and/or to isolate and identify other receptors or other cellular proteins further upstream or downstream in the signaling process(es) to which these novel proteins, analogs, fragments and derivatives bind, and hence, in whose function they are also involved.

A still further object of the invention is to provide inhibitors which can be introduced into cells to bind or interact with the novel proteins and possible isoforms thereof, which inhibitors may act to inhibit inflammation, cell death or survival processes when desired.

Moreover, it is an object of the present invention to use the above-mentioned novel proteins, isoforms and analogs, fragments and derivatives thereof as antigens for the preparation of polyclonal and/or monoclonal antibodies thereto. The antibodies, in turn, may be used, for example, for the purification of the new proteins from different sources, such as cell extracts or transformed cell lines.

Furthermore, these antibodies may be used for diagnostic purposes, e.g. for identifying possible disorders related to abnormal functioning of cellular effects mediated directly by caspases, kinases, proteins belonging to the BCL2 family, or TRAF proteins or mediated by the p55 TNF receptor, FAS/APO1 receptor, or other related receptors and their associated cellular proteins (e.g. RAIDD, MORT-1, TRADD, RIP), which act directly or indirectly to modulate/mediate intracellular processes via interaction with TRAF proteins, caspases, kinases, or members of the BCL2 family of proteins.

A further object of the invention is to provide pharmaceutical compositions comprising the above novel proteins, isoforms, or analogs, fragments or derivatives thereof, as well as pharmaceutical compositions comprising the above noted antibodies or other antagonists.

SUMMARY OF THE INVENTION

In accordance with the present invention, a new protein designated B1, (originally designated CBK for 'c-IAP-binding kinase', due to its having some homology with c-IAP, see Example 1 below, but, hereinafter will be called 'B1'), has been isolated which has a prodomain (CARD) region, a kinase domain and an intermediate region between said CARD and kinase domains, and hence is possibly involved in the modulation of inflammation, cell death and cell survival processes as detailed herein below. As is also explained herein below, the modulation by B1 of cell death or survival pathways may be positive (augmentory/enhancing) or negative (inhibitory) depending on the type of intracellular proteins with which it interacts.

Accordingly, the present invention provides a DNA sequence encoding a B1 protein, isoforms, fragments, or analogs thereof, said B1, isoforms, fragments or analogs thereof being capable of interacting with intracellular mediators or modulators of inflammation, cell death or cell survival pathways directly or indirectly, said B1, isoforms, fragments or analogs being intracellular modulators of said intracellular inflammation, cell death and/or cell survival pathways.

Embodiments of the above DNA sequence of the invention include:

(i) A DNA sequence selected from the group consisting of:
  (a) a cDNA sequence derived from the coding region of a native B1 protein;
  (b) a fragment of a sequence of (a) which encodes a biologically active protein capable of modulating the inflammation, cell death or cell survival pathway, or both;
  (c) a DNA sequence capable of hybridization to a sequence of (a) or (b) under moderately stringent conditions and which encodes a biologically active B1 protein, analog or fragment capable of modulating the intracellular inflammation, death or cell survival pathway, or both;
  (d) a DNA sequence which is degenerate as a result of the genetic code to the DNA sequences defined in (a)-(c) and which encodes a biologically active B1 protein, analog or fragment capable of modulating the inflammation, cell death or cell survival pathway or both.

(ii) A DNA sequence as above, comprising at least part of the sequence depicted in FIG. 3 and encoding at least one active B1 protein, isoform, analog or fragment.

(iii) A DNA sequence as above, encoding a B1 protein, isoform, analog or fragment having at least part of the amino acid sequence depicted in FIG. 3.

In another aspect, the invention provides a vector comprising any of the above DNA sequences of the invention, capable of being expressed in host cells selected from prokaryotic and eukaryotic cells; and the transformed prokaryotic and eukaryotic cells containing said vector.

By way of another aspect of the invention, there is provided a B1 protein, isoforms, fragments, functional analogs and derivatives thereof, encoded by a DNA sequence of the invention, as above, said protein, isoforms, fragments, analogs and derivatives thereof, possibly being capable of modulating the intracellular inflammation, cell death or cell survival pathways, or both, directly or indirectly, by association with other intracellular modulators or mediators of these pathways.

An embodiment of the protein of the invention is, a B1 protein, isoform, fragment, analogs and derivatives thereof, wherein said protein, isoform, analogs, fragments and derivatives have at least part of the amino acid sequence depicted in FIG. 3.

The invention also provides a method for producing a B1 protein, isoform, fragment, analog or derivative thereof, as above, which comprises growing the aforesaid transformed host cells under conditions suitable for the expression of said protein, isoform, fragment, analog or derivative thereof, effecting post-translational modification, as necessary, for obtaining said protein, isoform, fragment, analog or derivative thereof, and isolating said expressed protein, isoform, fragment, analog or derivative.

In a further aspect, the invention provides antibodies or active fragments or derivatives thereof, specific for the B1 protein, isoform, analog, fragment or derivative thereof of the invention.

In an additional aspect, the invention provides for various methods for the modulation of intracellular signaling pathways, for example, the following:

(i) a method for the modulation or mediation in cells of the activity of inflammation, cell death or cell survival pathways or any other intracellular signaling activity modulated or mediated directly or indirectly by B1 or by other molecules to which a B1 protein, isoform, analog, fragment or derivative thereof of the invention binds or otherwise interacts, directly or indirectly, said method comprising treating said cells by introducing into said cells one or more of said B1 protein, isoform, analog, fragment or derivative thereof in a form suitable for intracellular introduction thereof, or introducing into said cells a DNA sequence encoding said one or more B1 protein, isoform, analog, fragment or derivative thereof in the form of a suitable vector carrying said sequence, said vector being capable of effecting the insertion of said sequence into said cells in a way that said sequence is expressed in said cells.

(ii) a method as above, wherein said treating of cells comprises introducing into said cells a DNA sequence encoding said B1 protein, isoform, fragment, analog or derivative in the form of a suitable vector carrying said sequence, said vector being capable of effecting the insertion of said sequence into said cells in a way that said sequence is expressed in said cells.

(iii) a method as above, wherein said treating of said cells is by transfection of said cells with a recombinant animal virus vector comprising the steps of:
  (a) constructing a recombinant animal virus vector carrying a sequence encoding a viral surface protein (ligand) that is capable of binding to a specific cell surface receptor on the surface of said cells to be treated and a second sequence encoding a protein selected from said B1 protein, isoforms, analogs, fragments and derivatives as above, that when expressed in said cells is capable of modulating/mediating the activity of the inflammation, cell death or cell survival pathways, directly or indirectly, or any other intracellular signaling activity modulated/mediated by other intracellular molecules with which said B1 protein, isoforms, analogs, fragments and derivatives interact directly or indirectly; and
  (b) infecting said cells with said vector of (a).

(iv) a method for modulating the inflammation, cell death or cell survival pathways in cells which are modulated directly or indirectly by B1, comprising treating said cells with antibodies or active fragments or derivatives thereof, as above, said treating being by application of a suitable composition containing said antibodies, active fragments or derivatives thereof to said cells, wherein when the B1 protein or portions thereof of said cells are exposed on the extracellular surface, said composition is formulated for extracellular application, and when said B1 proteins are intracellular said composition is formulated for intracellular application.

(v) a method for modulating the inflammation, cell death, cell survival or other pathways in cells which are modulated directly or indirectly by B1, comprising treating said cells with an oligonucleotide sequence which is an antisense sequence for at least part of the DNA sequence encoding a B1 protein of the invention, said oligonucleotide sequence being capable of blocking the expression of the B1 protein.

(vi) a method as above wherein said oligonucleotide sequence is introduced to said cells via a virus noted in (ii) above, wherein said second sequence of said virus encodes said oligonucleotide sequence.

(vii) a method for modulating the inflammation, cell death, cell survival or other pathways in which cells are modulated directly or indirectly by B1, comprising applying the ribozyme procedure in which a vector encoding a ribozyme sequence capable of interacting with a cellular mRNA sequence encoding a B1 protein of the invention, is introduced into said cells in a form that permits expression of said ribozyme sequence in said cells, and wherein when said ribozyme sequence is expressed in said cells it interacts with said cellular mRNA sequence and cleaves said mRNA sequence resulting in the inhibition of expression of said B1 protein in said cells.

In a different aspect, the present invention provides for a method for isolating and identifying proteins, of the invention, having homology with or being capable of direct or indirect interactions with any proteins having a prodomain or caspase recruiting domain (CARD), or other proteins or enzymes involved in intracellular signaling, via the kinase or intermediate domains present in the proteins of the invention, comprising applying the yeast two-hybrid procedure in which a sequence encoding said protein with said CARD, kinase, and intermediate domains, or at least one of these domains, is carried by one hybrid vector and a sequence from a cDNA or genomic DNA library is carried by the second hybrid vector, the vectors then being used to transform yeast host cells and the positive transformed cells being isolated, followed by extraction of the said second hybrid vector to obtain a sequence encoding a protein which binds to said CARD-, kinase-, and/or intermediate domain-containing protein.

In a yet further aspect of the present invention, there is provided a pharmaceutical composition for the modulation of the inflammation, cell death, cell survival or other pathways in cells which are modulated directly or indirectly by B1, comprising, as active ingredient, at least one B1 protein, of the invention, its biologically active fragments, analogs, derivatives or mixtures thereof.

An embodiment of the above pharmaceutical composition is one for modulating the inflammation, cell death, cell survival or other pathways in cells which are modulated directly or indirectly by B1 comprising as active ingredient, a recombinant animal virus vector encoding a protein capable of binding a cell surface receptor and encoding at least one B1 protein, isoform, active fragments or analogs.

Another embodiment of the above pharmaceutical composition is one for modulating the inflammation, cell death, cell survival or other pathways in cells which are modulated directly or indirectly by B1, comprising as active ingredient, an oligonucleotide sequence which is an anti-sense sequence of the B1 protein mRNA sequence.

A further embodiment of the above pharmaceutical composition is one for the prevention or treatment of a pathological condition associated with the regulation of apoptosis by one or more molecules to which a B1 protein binds directly or indirectly, said composition comprising an effective amount of a B1 protein or a DNA molecule coding therefor, or a molecule capable of disrupting the direct or indirect interaction of said B1 protein with one or more molecules to which a B1 protein binds or with which it interacts.

A still further embodiment of the above pharmaceutical composition is one for the prevention or treatment of a pathological condition associated with the regulation of apoptosis by one or more molecules to which a B1 protein binds directly or indirectly, said composition comprising an effective amount of a B1 protein, isoform, fragment, analog or derivative thereof, or a DNA molecule coding therefor, or a molecule capable of disrupting the direct or indirect interaction of said B1 protein, isoform, fragment, analog or derivative thereof with one or more molecules to which said B1 protein, isoform, fragment, analog or derivative binds.

An additional embodiment of the above pharmaceutical composition is one for the prevention or treatment of a pathological condition associated with the regulation of apoptosis by one or more molecules to which the B1 protein binds directly or indirectly, said composition comprising a molecule capable of interfering with the protein kinase activity of B1.

In another different aspect of the invention there are provided therapeutic methods as follows:
  (i) A method for the prevention or treatment of a pathological condition associated with the regulation of apoptosis by one or more molecules to which a B1 protein binds directly or indirectly, said method comprising administering to a patient in need an effective amount of a protein or isoform, fragment, analog and derivative thereof or a mixture of any thereof, or a DNA molecule coding therefor, or a molecule capable of disrupting the direct or indirect interaction of said B1 protein or isoform, fragment, analog and derivative thereof or a mixture of any thereof with one or more molecules to which said B1 protein or isoform, fragment, analog and derivative thereof or a mixture of any thereof binds directly or indirectly.
  (ii) A method of modulating inflammation processes, apoptopic processes or programmed cell death processes (cell death pathways) in which the B1 protein is involved directly or indirectly, comprising treating said cells with one or more B1 proteins, isoforms, analogs, fragments or derivatives, wherein said treating of said cells comprises introducing into said cells said one or more B1 proteins, isoforms, analogs, fragments or derivatives in a form suitable for intracellular introduction thereof, or introducing into said cells a DNA sequence encoding said one or more B1 proteins, isoforms, analogs, fragments or derivatives in the form of a suitable vector carrying said sequence, said vector being capable of effecting the insertion of said sequence into said cells in a way that said sequence is expressed in said cells.
  (iii) A method of modulating cell survival processes in which the B1 protein is involved directly or indirectly, comprising treating said cells with one or more B1 proteins, isoforms, analogs, fragments or derivatives, wherein said treating of cells comprises introducing into said cells said one or more B1 proteins, isoforms, analogs, fragments or derivatives in a form suitable for intracellular introduction thereof, or introducing into said cells a DNA sequence encoding said one or more B1 proteins, isoforms, analogs, fragments or derivatives in the form of a suitable vector carrying said sequence, said vector being capable of effecting the insertion of said sequence into said cells in a way that said sequence is expressed in said cells.

A still further aspect of the present invention, the following screening methods and methods for the identification and production of various ligands are provided:
  (i) A method for screening of a ligand capable of binding to a B1 protein comprising contacting an affinity chromatography matrix to which said protein is attached with a cell extract whereby the ligand is bound to said matrix, and eluting, isolating and analyzing said ligand.
  (ii) A method for screening of a DNA sequence coding for a ligand capable of binding to a B1 protein, comprising applying the yeast two-hybrid procedure in which a sequence encoding said B1 protein is carried by one hybrid vector and sequences from a cDNA or genomic DNA library are carried by the second hybrid vector, transforming yeast host cells with said vectors, isolating the positively transformed cells, and extracting said second hybrid vector to obtain a sequence encoding said ligand.
  (iii) A method for identifying and producing a ligand capable of modulating the cellular activity modulated/mediated by B1 comprising:
    a) screening for a ligand capable of binding to a polypeptide comprising at least a portion of B1 having at least some of the amino acid residues of B1 depicted in FIG. 3, which include essentially all of the prodomain (or CARD) of B1;
    b) identifying and characterizing a ligand, other than BCL2, TRAF2, or portions of a receptor of the TNF/NGF receptor family or other known proteins having a prodomain (CARD), found by said screening step to be capable of said binding; and
    c) producing said ligand in substantially isolated and purified form.
  (iv) A method for identifying and producing a ligand capable of modulating the cellular activity modulated or mediated by a B1 protein comprising:
    a) screening for a ligand capable of binding to a polypeptide comprising at least the carboxy terminal portion of the B1 sequence depicted in FIG. 3 including the prodomain (CARD);
    b) identifying and characterizing a ligand, other than BCL2, TRAF2, or portions of a receptor of the TNF/NGF receptor family or other known proteins having a prodomain (CARD), found by said screening step to be capable of said binding; and
    c) producing said ligand in substantially isolated and purified form.
  (v) A method for identifying and producing a ligand capable of modulating the cellular activity modulated/mediated by B1 comprising:
    a) screening for a ligand capable of binding to at least the N-terminal portion of the B1 sequence depicted in FIG. 3 including substantially all of the kinase domain of B1;
    b) identifying and characterizing a ligand, other than BCL2, TRAF2, or portions of a receptor of the TNF/NGF receptor family or other known intracellular modulatory proteins, found by said screening step to be capable of said binding; and
    c) producing said ligand in substantially isolated and purified form.

(vi) A method for identifying and producing a molecule capable of directly or indirectly modulating the cellular activity modulated/mediated by B1 comprising:
   a) screening for a molecule capable of modulating activities modulated/mediated by B1;
   b) identifying and characterizing said molecule; and
   c) producing said molecule in substantially isolated and purified form.

(vii) A method for identifying and producing a molecule capable of directly or indirectly modulating the cellular activity modulated/mediated by a protein of the invention, comprising:
   a) screening for a molecule capable of modulating activities modulated/mediated by a protein of the invention;
   b) identifying and characterizing said molecule; and
   c) producing said molecule in substantially isolated and purified form.

Other aspects of the invention will be apparent from the following Detailed Description of the Invention.

BRIEF DESCRIPTION OF THE DRAWINGS

FIG. 3 (A,B) shows schematically the deduced amino acid sequence (A) (SEQ ID NO:1) of the B1 protein of the present invention and the determined nucleotide sequence coding therefor (B) (SEQ ID NO:2), wherein in the amino acid sequence is shown the kinase domain of B1 (boxed region at N-terminal end) and the CARD domain of B1 (underlined region at C-terminal end).

FIG. 6 shows NF-kB activation results of measurements carried out with the different constructs of FIG. 6 and example 3;

DETAILED DESCRIPTION OF THE INVENTION

Figure 1:
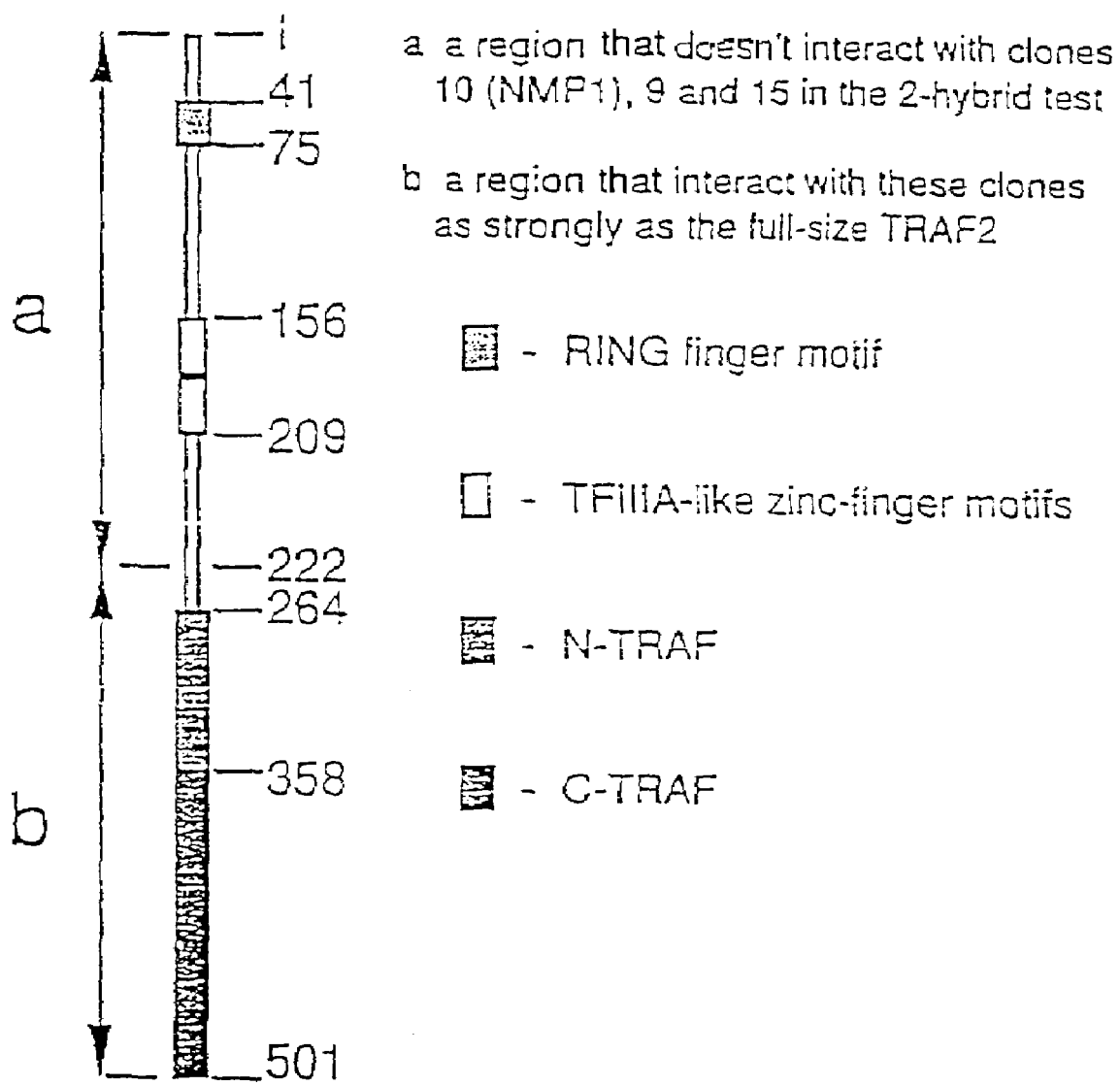
FIG. 1 shows a diagrammatic illustration of the structure of the TRAF2 molecule.

The present invention relates, in one aspect to a new B1 protein which has a prodomain or CARD domain (caspase recruiting domain) and which has a protein kinase domain of similarity to the RIP-kinase domain. As such the B1 protein of the present invention is possibly capable of interacting with a number of intracellular proteins involved in the inflammation, cell death (apoptosis) and cell survival (NF-κB activation) pathways. This interaction may be by binding various proteins or otherwise interacting with them via the prodomain (CARD), or it may be by way of the activity of the kinase domain, or both of these types of interaction may occur at the same time. For example, B1 may be able to recruit a number of proteins having prodomains (CARDs) and then to phosphorylate them via its kinase domain. Likewise, B1 may serve in some instances as a docking or recruiting protein via its prodomain (CARD) for various other prodomain-containing proteins, which may not be substrates for the kinase domain of B1, or B1 may interact with various proteins only through its kinase domain and not via its CARD domain.

In addition, as is detailed herein, binding assay results indicate that the new B1 protein of the invention is possibly capable of binding to the BCL2 protein. This finding raises the possibility that the B1 protein may be a regulator of BCL2 activity, especially as concerns the regulation of apoptosis. In initial biological activity analyses, the possibility also arises that the B1 protein may inhibit the protective effect of BCL2 against apoptosis. This in view of the observations that the B1 protein on its own does not cause cell death, but acts to enhance cell death when added to cells with other inducers of cell death such as, for example, FAS-R, p55 TNF-R and RIP (said addition to cells by co-transformation with vectors capable of expressing in the cells B1, FAS-R, p55 TNF-R or RIP, see Example 2 below). Hence, the possibility arises that B1 may not act in an analogous way to BAX or BAK, which on their own, in the form of homodimers, can cause cell death (see 'Background' section above), but rather, B1 may possibly act in an analogous way to BAD which serves to negatively regulate BCL2 by binding BCL2 and preventing its binding to BAX or BAK thereby resulting in more free BAX and/or BAK which, in turn, cause increased cell death (see 'Background' section above).

Moreover, with respect to the above noted activation of NF-κB and cell survival, B1 may possibly also achieve its observed activity of enhancing cell death by way of possibly causing a reduction in NF-κB activation, maybe by way of B1's kinase activity which may possibly serve to modulate various proteins (e.g. NIK) necessary for induction of NF-κB activation, with the result that reduced NF-κB activation will occur and subsequently cell survival will be reduced. In this respect it is interesting to note that when B1 is added with inducers of cell death such as FAS-R, p55 TNF-R or RIP it enhances their cell killing activity. It is known that both p55 TNF-R and FAS-R, and possibly also RIP besides inducing the cell death pathways culminating in increased caspase activity, also induce activation of NF-κB which, to some extent, negates the induced cell death. In some cells it has even been observed that TNF does not kill the cells, this being attributed to the induction of NF-κB activation by the TNF receptors and not the failure of the co-induced cell death pathways by these receptors, so that in these cells the NF-κB-mediated cell survival pathways are apparently more active than the cell death pathways. Thus, by blocking NF-κB induction it would be possible to enhance the cell killing mediated by, for example, FAS-R, p55 TNF, RIP, and the B1 protein of the invention may possibly serve this function and give rise to its observed enhancement of cell death when added with FAS-R, p55-TNF-R or RIP.

In view of the above, it arises that B1 may possibly regulate inflammation, cell death or cell survival processes in a number of ways, and may even do so simultaneously. For example, B1 may possibly inhibit NF-κB activation, or B1 may possibly even act on other intracellular proteins involved in the cell death or cell survival pathways independently of its possible effects on NF-κB or in addition to its possible effects on NF-κB.

Hence, B1 appears to possibly have the capability to modulate a wide range of intracellular proteins, in particular, those involved in the inflammation, cell death and cell survival pathways. As is detailed herein below, a number of known intracellular proteins have prodomains (CARDs), such as, for example, various caspase enzymes involved in the proteolytic destruction of cells (cell death pathway) including ICE, ICH-1, Mch6 and others, as well as various adaptor proteins also involved in cell death pathways including RAIDD, c-IAP1, c-IAP2 and others. In this way B1 may possibly interact directly or indirectly with various caspases via their common CARDs and thereby possibly modulate their activity. This modulation may be positive, namely, B1 may possibly serve to concentrate various caspases and thereby enhance their proteolytic activity leading to increased cell death. Further, B1 was isolated using the sequence of c-IAP1 and B1 shares homology with c-IAP1, which itself is an inhibitor of apoptosis. c-IAP1 has a prodomain (CARD) and may inhibit apoptosis by recruiting caspases thereby preventing their activity. B1 may therefore possibly interact directly or indirectly with c-IAP1 and lead to a suppression of its inhibition of apoptosis, thereby resulting in increased cell death. Moreover, B1 possibly by indirectly or direct interaction with various caspases via its CARD, may also be able to modulate them by phosphorylation via its kinase domain, and in this way B1 may enhance the caspase activity.

In a more indirect fashion, B1 by possibly being able to interact indirectly or directly with adaptor proteins such as RAIDD, c-IAP1, c-IAP2 and others having CARDs can thereby possibly interact with other proteins more upstream in the inflammation, cell death and cell survival pathways. For example, RAIDD interacts with other intracellular proteins such as RIP and TRADD via common death domains, which, in turn interact with proteins such as MORT-1, the p55-TNF-R and FAS-R. In this way, by possibly interacting with RAIDD, B1 is thus possibly indirectly linked to these death-effecting receptors and proteins. Similarly, c-IAP1 and c-IAP2 interact with the TRAF2 protein, which, in turn, interacts with the p75-TNF-R, and with MORT-1, p55-TNF-R and FAS-R via the interaction between TRAF2 and REP as well as TRADD. Accordingly, B1 may possibly be an indirect modulator of cell death processes by being indirectly linked to the above noted adaptor proteins, effector proteins and receptors. This indirect modulation may be positive, i.e., it may lead to enhanced cell death.

Moreover, by virtue of B1 possibly being able to interact at least indirectly (via c-IAP1) with TRAF2 raises the possibility of the involvement of B1 in the cell survival pathway which is associated with the induction of NF-κB activation. It is now known that TRAF2 binds directly to NIK (Malinin et al., 1997), which is directly involved in the induction of NF-κB activation and thereby cell survival. Accordingly, by possibly being able to modulate TRAF2 indirectly, B1 may be capable of modulating the cell survival pathway as well. Further, by virtue of its kinase domain B1 may possibly be even more directly involved in the MAP kinase pathway (to which NIK belongs) leading to induction of NF-κB activation and cell survival. However, as noted above, in view of the fact that B1 leads to an enhancement of cell death, it may be that B1 has a negative role in the modulation of the cell survival process, namely, B1 may possibly modulate TRAF2 or B1 may possibly be directly involved in the MAP kinase pathway but in a way that leads to reduced NF-κB activation.

It is also possible that B1 plays a central role in the modulation of intracellular signaling pathways, in particular, the inflammation cell death and cell survival pathways, and as such B1 may serve to modulate these in a way that may shift the balance from cell survival to cell death induction in agreement with the observed (see Example 2) enhancing effect B1 has on cell death induction. B1 may thus be considered as a 'modulator of intracellular signaling' activity directly or indirectly on various component proteins making up these pathways.

Thus, when considering the various possible uses of B1 therapeutically, it is important to understand that in all cases B1 may have multiple roles, namely, it may enhance cell death processes, and at the same time it may possibly actively inhibit the induction of NF-κB and hence inhibit the cell survival pathway, or depending on the actual proteins/enzymes to which B1 binds and their relative amounts in the cell, B1 may possibly, in some cells, act to inhibit cell survival pathways, and in others, may possibly act to enhance cell death pathways by suppressing cell death inhibitors.

Therefore, in general, as will arise from the following, when it is desired to increase cell death, e.g. in tumors, HIV-infected cells and the like, it may be possible to use B1 to achieve this goal. For example, B1 may be administered to the cells directly or a DNA molecule encoding B1 may be introduced into the cells to increase B1 expression.

Likewise, in situations in which it is desired to save cells from cell death induced by TNF or FAS-ligand, for example, in various inflammations, autoimmune diseases, graft-vs-host reactions and the like, and instead promote cell survival, then B1 antagonists may possibly be used to achieve this goal. For example, B1 antagonists may be administered, such as, anti-B1 antibodies, oligonucleotides having antisense B1 sequences, ribozymes with B1 sequences, or various peptides or organic molecules designed specifically to inhibit B1 activity.

Hence, when the uses of B1 are noted herein below, they will be set forth in terms of the modulatory effects of B1 on various intracellular processes or diseases, and it is to be understood in view of the above mentioned that this modulation may be positive (augmentory) as is the case when considering cell death pathways, or negative (inhibitory) as is the case when considering cell survival pathways.

The present invention also concerns the DNA sequences encoding biologically active B1 proteins, as well as DNA sequences encoding biologically active analogs, fragments and derivatives thereof, and the B1 proteins, analogs, fragments and derivatives of the proteins encoded by the DNA sequences. The preparation of such analogs, fragments and derivatives is by standard procedures (see for example, Sambrook et al., 1989) in which in the DNA encoding sequences, one or more codons may be deleted, added or substituted by another, to yield encoded analogs having at least a one amino acid residue change with respect to the native protein. Acceptable analogs are those which retain at least the prodomain (CARD) or kinase domain of B1 or at least active portions of either or both of these domains, with or without mediating any other binding or enzymatic activity, i.e. do not bind or otherwise interact, directly or indirectly, to a further downstream protein or other factor, or do not catalyze a signal-dependent reaction (e.g. kinase reaction). In such a way analogs can be produced which have a so-called dominant-negative effect, namely, an analog which is defective either in binding to or otherwise interacting with other proteins via the prodomain, or in subsequent signaling (also possibly kinase activity) following such binding as noted above. Such analogs can be used, for example, to modulate the inflammation, cell death or survival pathways as noted above, by competing with the natural B1 proteins. Likewise, so-called dominant-positive analogs may be produced which would serve to enhance the B1 effect. These would have the same or better B1-related binding properties to the other proteins and the same or better signaling properties or kinase activities of the natural B1 proteins. In an analogous fashion, biologically active fragments of the clones of the invention may be prepared as noted above with respect to the preparation of the analogs. Suitable fragments of the DNA sequences of the invention are those which encode a protein or polypeptide retaining the B1 binding capability to other proteins or which can mediate any other binding or enzymatic (kinase) activity as noted above. Accordingly, fragments of the encoded proteins of the invention can be prepared which have a dominant-negative or a dominant-positive effect as noted above with respect to the analogs. Similarly, derivatives may be prepared by standard modifications of the side groups of one or more amino acid residues of the proteins, their analogs or fragments, or by conjugation of the proteins, their analogs or fragments, to another molecule e.g. an antibody, enzyme, receptor, etc., as are well known in the art.

Of the above DNA sequences of the invention which encode a B1 protein, isoform, analog, fragment or derivative, there is also included, as an embodiment of the invention, DNA sequences capable of hybridizing with a cDNA sequence derived from the coding region of a native B1 protein, in which such hybridization is performed under moderately stringent conditions, and which hybridizable DNA sequences encode a biologically active B1 protein. These hybridizable DNA sequences therefore include DNA sequences which have a relatively high homology to the native B1's cDNA sequence, and as such represent B1-like sequences which may be, for example, naturally-derived sequences encoding the various B1 protein isoforms, or naturally-occurring sequences encoding proteins belonging to a group of B1-like sequences encoding a protein having the activity of B1 proteins. Further, these sequences may also, for example, include non-naturally occurring, synthetically produced sequences, that are similar to the native B1 protein cDNA sequence but incorporate a number of desired modifications. Such synthetic sequences therefore include all of the possible sequences encoding analogs, fragments and derivatives of B1 proteins, all of which have the activity of B1 proteins.

To obtain the various above noted naturally occurring B1 protein-like sequences, standard procedures of screening and isolation of naturally-derived DNA or RNA samples from various tissues may be employed using the natural B1 protein cDNA or portion thereof as probe (see for example standard procedures set forth in Sambrook et al., 1989).

Likewise, to prepare the above noted various synthetic B1 protein-like sequences encoding analogs, fragments or derivatives of B1 proteins, a number of standard procedures may be used as are detailed herein below concerning the preparation of such analogs, fragments and derivatives.

A polypeptide or protein "substantially corresponding" to B1 protein includes not only B1 protein but also polypeptides or proteins that are analogs of B1 protein.

Analogs that substantially correspond to B1 protein are those polypeptides in which one or more amino acid of the B1 protein's amino acid sequence has been replaced with another amino acid, deleted and/or inserted, provided that the resulting protein exhibits substantially the same or higher biological activity as the B1 protein to which it corresponds.

In order to substantially correspond to B1 protein, the changes in the sequence of B1 proteins, such as isoforms are generally relatively minor. Although the number of changes may be more than ten, preferably there are no more than ten changes, more preferably no more than five, and most preferably no more than three such changes. While any technique can be used to find potentially biologically active proteins which substantially correspond to B1 proteins, one such technique is the use of conventional mutagenesis techniques on the DNA encoding the protein, resulting in a few modifications. The proteins expressed by such clones can then be screened for their ability to bind to various other proteins having, for example, prodomains (CARD), kinase binding sites, or to B1 itself, and to modulate the activity of these other proteins or B1 itself in the modulation/mediation of the intracellular pathways noted above.

"Conservative" changes are those changes which would not be expected to change the activity of the protein and are usually the first to be screened as these would not be expected to substantially change the size, charge or configuration of the protein and thus would not be expected to change the biological properties thereof.

Conservative substitutions of B1 proteins include an analog wherein at least one amino acid residue in the polypeptide has been conservatively replaced by a different amino acid. Such substitutions preferably are made in accordance with the following list as presented in Table IA, which substitutions may be determined by routine experimentation to provide modified structural and functional properties of a synthesized polypeptide molecule while maintaining the biological activity characteristic of B1 protein.

TABLE IA

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Alternatively, another group of substitutions of B1 protein are those in which at least one amino acid residue in the polypeptide has been removed and a different residue inserted in its place according to the following Table IB. The types of substitutions which may be made in the polypeptide may be based on analysis of the frequencies of amino acid changes between a homologous protein of different species, such as those presented in Table 1-2 of Schulz et al., G. E., Principles of Protein Structure Springer-Verlag, New York, N.Y., 1798, and FIGS. 3-9 of Creighton, T. E., Proteins: Structure and Molecular Properties, W.H. Freeman & Co., San Francisco, Calif. 1983. Based on such an analysis, alternative conservative substitutions are defined herein as exchanges within one of the following five groups:

TABLE IB

| | |
|---|---|
| 1. | Small aliphatic, nonpolar or slightly polar residues: Ala, Ser, Thr (Pro, Gly); |
| 2. | Polar negatively charged residues and their amides: Asp, Asn, Glu, Gln; |
| 3. | Polar, positively charged residues: His, Arg, Lys; |
| 4. | Large aliphatic nonpolar residues: Met, Leu, Ile, Val (Cys); and |
| 5. | Large aromatic residues: Phe, Tyr, Trp. |

The three amino acid residues in parentheses above have special roles in protein architecture. Gly is the only residue lacking any side chain and thus imparts flexibility to the chain. This however tends to promote the formation of secondary structure other than α-helical. Pro, because of its unusual geometry, tightly constrains the chain and generally tends to promote 3-turn-like structures, although in some cases Cys can be capable of participating in disulfide bond formation which is important in protein folding. Note that Schulz et al., supra, would merge Groups 1 and 2, above. Note also that Tyr, because of its hydrogen bonding potential, has significant kinship with Ser, and Thr, etc.

Conservative amino acid substitutions according to the present invention, e.g., as presented above, are known in the art and would be expected to maintain biological and structural properties of the polypeptide after amino acid substitution. Most deletions and substitutions according to the present invention are those which do not produce radical changes in the characteristics of the protein or polypeptide molecule. "Characteristics" is defined in a non-inclusive manner to define both changes in secondary structure, e.g. α-helix or β-sheet, as well as changes in biological activity, e.g., binding to other proteins with prodomains (CARD), or kinase activity and/or modulation of cell death or survival pathways as noted above and below.

Examples of production of amino acid substitutions in proteins which can be used for obtaining analogs of B1 proteins for use in the present invention include any known method steps, such as presented in U.S. Pat. RE 33,653, U.S. Pat. Nos. 4,959,314, 4,588,585 and 4,737,462, to Mark et al.; U.S. Pat. No. 5,116,943 to Koths et al., U.S. Pat. No. 4,965,195 to Namen et al.; U.S. Pat. No. 4,879,111 to Chong et al.; and U.S. Pat. No. 5,017,691 to Lee et al.; and lysine substituted proteins presented in U.S. Pat. No. 4,904,584 (Shaw et al.).

Besides conservative substitutions discussed above which would not significantly change the activity of B1 protein, either conservative substitutions or less conservative and more random changes, which lead to an increase in biological activity of the analogs of B1 proteins, are intended to be within the scope of the invention.

When the exact effect of the substitution or deletion is to be confirmed, one skilled in the art will appreciate that the effect of the substitution(s), deletion(s), etc., will be evaluated by routine binding and cell death assays. Screening using such a standard test does not involve undue experimentation.

At the genetic level, these analogs are generally prepared by site-directed mutagenesis of nucleotides in the DNA encoding the B1 protein, thereby producing DNA encoding the analog, and thereafter synthesizing the DNA and expressing the polypeptide in recombinant cell culture. The analogs typically exhibit the same or increased qualitative biological activity as the naturally occurring protein, Ausubel et al., *Current Protocols in Molecular Biology*, Greene Publications and *Wiley Interscience*, New York, N.Y., 1987-1995; Sambrook et al., Molecular Cloning: A Laboratory Manual, Cold Spring Harbor Laboratory, Cold Spring Harbor, N.Y., 1989.

Preparation of a B1 protein in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared analog or a native version of B1 protein. Site-specific mutagenesis allows the production of analogs through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al. *Third Cleveland Symposium on Macromolecules and Recombinant DNA*, Editor A. Walton, Elsevier, Amsterdam (1981), the disclosure of which is incorporated herein by reference. These phages are readily available commercially and their use is generally well known to those skilled in the art. Alternatively, plasmid vectors that contain a single-stranded phage origin of replication (Veira et al., *Meth. Enzymol.* 153:3, 1987) may be employed to obtain single-stranded DNA.

In general, site-directed mutagenesis in accordance herewith is performed by first obtaining a single-stranded vector that includes within its sequence a DNA sequence that encodes the relevant polypeptide. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated B1 protein sequence may be removed and placed in an appropriate vector, generally a transfer or expression vector of the type that may be employed for transfection of an appropriate host.

Accordingly, gene or nucleic acid encoding for a B1 protein can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a prolactin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding the B1 protein or a fragment thereof to be custom designed for ligation other sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; 4,795,699 and 4,921,794 to Tabor et al.; 5,142,033 to Innis; 5,122,464 to Wilson et al.; 5,091,310 to Innis; 5,066,584 to Gyllensten et al.; 4,889,818 to Gelfand et al.; 4,994,370 to Silver et al.; 4,766,067 to Biswas; 4,656,134 to Ringold; and Innis et al., eds., *PCR Protocols: A Guide to Method and Applications*) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991)), the entire contents of which patents and reference are entirely incorporated herein by reference.

In an analogous fashion, biologically active fragments of B1 or its isoforms may be prepared as noted above with respect to the analogs of B1 proteins. Suitable fragments of B1 proteins are those which retain at least the prodomain-related binding ability or the kinase activity and which can mediate the biological activity of the various other proteins or intracellular pathways associated with B1 proteins directly or indirectly. Accordingly, B1 protein fragments can be prepared which have a dominant-negative or a dominant-positive effect as noted above with respect to the analogs. It should be noted that these fragments represent a special class of the analogs of the invention, namely, they are defined portions of B1 proteins derived from the full B1 protein sequence, each such portion or fragment having any of the above-noted desired activities. Such fragment may be, e.g., a peptide.

Similarly, derivatives may be prepared by standard modifications of the side groups of one or more amino acid residues of the B1 protein, its analogs or fragments, or by conjugation of the B1 protein, its analogs or fragments, to another molecule e.g. an antibody, enzyme, receptor, etc., as are well known in the art. Accordingly, "derivatives" as used herein covers derivatives which may be prepared from the functional groups which occur as side chains on the residues or the N- or C-terminal groups, by means known in the art, and are included in the invention. Derivatives may have chemical moieties such as carbohydrate or phosphate residues, provided such a fraction has the same or higher biological activity as B1 proteins.

For example, derivatives may include aliphatic esters of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (for example that of seryl or threonyl residues) formed with acyl moieties.

The term "derivatives" is intended to include only those derivatives that do not change one amino acid to another of the twenty commonly occurring natural amino acids.

A B1 protein is a protein or polypeptide, i.e. a sequence of amino acid residues. A polypeptide consisting of a larger sequence which includes the entire sequence of a B1 protein, in accordance with the definitions herein, is intended to be included within the scope of such a polypeptide as long as the additions do not affect the basic and novel characteristics of the invention, i.e., if they either retain or increase the biological activity of the B1 protein or can be cleaved to leave a protein or polypeptide having the biological activity of the B1 protein. Thus, for example, the present invention is intended to include fusion proteins of the B1 protein with other amino acids or peptides.

The new B1 proteins, their analogs, fragments and derivatives have a number of possible uses as noted above and below, for example:

(i) They may be used to modulate cell survival pathways via direct or indirect modulation of the intracellular proteins to which they bind. In situations where an enhanced activity of these pathways is not desired, i.e. it is desired to inhibit them in favor of cell death pathways, for example, such as in anti-tumor or immuno-stimulatory applications, then it is desired that this modulation, by B1, its isoforms, analogs, fragments or derivatives be inhibitory. In this case the proteins of the invention, their analogs, fragments or derivatives, when they are inhibitory for cell survival pathways, may be introduced to the cells by standard procedures known per se. For example, as the proteins encoded by the DNA clones of the invention are intracellular and they should be introduced only into the cells where desired, a system for specific introduction of these proteins into the cells is necessary. One way of doing this is by creating a recombinant animal virus e.g. one derived from Vaccinia, to the DNA of which the following two genes will be introduced: the gene encoding a ligand that binds to cell surface proteins specifically expressed by the cells e.g. ones such as the AIDs (HIV) virus gp120 protein which binds specifically to some cells (CD4 lymphocytes and related leukemias) or any other ligand that binds specifically to cells carrying a known receptor, such that the recombinant virus vector will be capable of binding such cells; and the gene encoding the proteins of the invention. Thus, expression of the cell-surface-binding protein on the surface of the virus will target the virus specifically to the tumor cell or other receptor-carrying cell, following which the proteins encoding sequences will be introduced into the cells via the virus, and once expressed in the cells will result in inhibition of the cell survival pathways leading to a desired cell death or immuno-stimulatory effect in these cells. Construction of such recombinant animal virus is by standard procedures (see for example, Sambrook et al., 1989). Another possibility is to introduce the sequences of the encoded proteins in the form of oligonucleotides which can be absorbed by the cells and expressed therein.

Similarly, when the B1 proteins, isoforms, analogs, fragments or derivatives are stimulatory or otherwise enhance cell death processes, then they may also be administered to cells as above to provide increased anti-tumor, immunostimulatory or other cell death activity.

(ii) They may be used to enhance or augment the cell survival pathways, or, e.g. in cases such as tissue damage as in AIDS, septic shock or graft-vs.-host rejection, in which it is desired to block the cell death pathways or stimulate the cell survival pathways. In this situation it is possible, when the B1 proteins actually inhibit cell survival processes, or are stimulatory or otherwise augment cell death pathways, to, for example, introduce into the cells, by standard procedures, oligonucleotides having the anti-sense coding sequence for the B1 proteins of the invention, which would effectively block the translation of mRNAs encoding the proteins and thereby block their expression and lead to the inhibition of the (cell death) undesired effect. Such oligonucleotides may be introduced into the cells using the above recombinant virus approach, the second sequence carried by the virus being the oligonucleotide sequence.

Another possibility is to use antibodies specific for the proteins of the invention to inhibit their intracellular signaling activity.

Yet another way of inhibiting the undesired effect is by the recently developed ribozyme approach. Ribozymes are catalytic RNA molecules that specifically cleave RNAs. Ribozymes may be engineered to cleave target RNAs of choice, e.g. the mRNAs encoding the B1 proteins of the invention. Such ribozymes would have a sequence specific for the mRNA of the proteins and would be capable of interacting therewith (complementary binding) followed by cleavage of the mRNA, resulting in a decrease (or complete loss) in the expression of the proteins, the level of decreased expression being dependent upon the level of ribozyme expression in the target cell. To introduce ribozymes into the cells of choice (e.g. those carrying the sequence of the B1 proteins) any suitable vector may be used, e.g. plasmid, animal virus (retrovirus) vectors, that are usually used for this purpose (see also (i) above, where the virus has, as second sequence, a cDNA encoding the ribozyme sequence of choice). (For reviews, methods etc. concerning ribozymes see Chen et al., 1992; Zhao and Pick, 1993).

(iii) They may be used to isolate, identify and clone other proteins which are capable of binding to them, e.g. other proteins involved in the intracellular inflammation, cell death or cell survival pathways. For example, the DNA sequences encoding the proteins of the invention may be used in the yeast two-hybrid system in which the encoded proteins will be used as "bait" to isolate, clone and identify from cDNA or genomic DNA libraries other sequences ("preys") encoding proteins which can bind to the clones proteins. In the same way, it may also be determined whether the proteins of the present invention can bind to other cellular proteins, e.g. other receptors of the TNF/NGF superfamily of receptors, or other members of the BCL2 family.

(iv) The encoded proteins, their analogs, fragments or derivatives may also be used to isolate, identify and clone other proteins of the same class i.e. those having prodomains (CARDs) or kinase domains, or to functionally related proteins, and involved in the intracellular signaling process. In this application the above noted yeast two-hybrid system may be used, or there may be used a recently developed system employing non-stringent Southern hybridization followed by PCR cloning (Wilks et al., 1989).

(v) Yet another approach to utilize the encoded proteins of the invention, their analogs, fragments or derivatives is to use them in methods of affinity chromatography to isolate and identify other proteins or factors to which they are capable of binding, e.g., proteins related to B1 proteins or other proteins or factors involved in the intracellular signaling process. In this application, the proteins, their analogs, fragments or derivatives of the present invention, may be individually attached to affinity chromatography matrices and then brought into contact with cell extracts or isolated proteins or factors suspected of being involved in the intracellular signaling process. Following the affinity chromatography procedure, the other proteins or factors which bind to the proteins, their analogs, fragments or derivatives of the invention, can be eluted, isolated and characterized.

(vi) As noted above, the proteins, their analogs, fragments or derivatives of the invention may also be used as immunogens (antigens) to produce specific antibodies thereto. These antibodies may also be used for the purposes of purification of the proteins of the invention either from cell extracts or from transformed cell lines producing them, their analogs or fragments. Further, these antibodies may be used for diagnostic purposes for identifying disorders related to abnormal functioning of the receptor system or inflammation, cell death or survival pathways in which they function. Thus, should such disorders be related to a malfunctioning intracellular signaling system involving the proteins of the invention, such antibodies would serve as an important diagnostic tool. The term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof, such as, for example, Fab and $F(ab')_2$-fragments lacking the Fc fragment of intact antibody, which are capable of binding antigen.

(vii) The antibodies, including fragments of antibodies, useful in the present invention may be used to quantitatively or qualitatively detect the clones of the invention in a sample, or to detect presence of cells which express the clones of the present invention. This can be accomplished by immunofluorescence techniques employing a fluorescently labeled antibody coupled with light microscopic, flow cytometric, or fluorometric detection.

The antibodies (or fragments thereof) useful in the present invention may be employed histologically, as in immunofluorescence or immunoelectron microscopy, for in situ detection of the clones of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the clones, but also its distribution on the examined tissue. Using the present invention, those of ordinary skill will readily perceive that any of wide variety of histological methods (such as staining procedures) can be modified in order to achieve such in situ detection.

Such assays for the clones of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capably of identifying the encoded proteins, and detecting the antibody by any of a number of techniques well known in the art.

(viii) The encoded proteins of the invention may also be used as indirect modulators of a number of other proteins by virtue of their capability of binding to other intracellular proteins, which other intracellular proteins directly bind yet other intracellular proteins or an intracellular domain of a transmembrane protein.

For the purposes of modulating these other intracellular proteins or the intracellular domains of transmembranal proteins, the proteins of the invention may be introduced into cells in a number of ways as mentioned hereinabove in (i) and (ii).

It should also be noted that the isolation, identification and characterization of the proteins of the invention may be performed using any of the well known standard screening procedures. For example, one of these screening procedures, the yeast two-hybrid procedure which was used to identify the proteins of the invention. Likewise other procedures may be employed such as affinity chromatography, DNA hybridization procedures, etc. as are well known in the art, to isolate, identify and characterize the proteins of the invention or to isolate, identify and characterize additional proteins, factors, receptors, etc. which are capable of binding to the proteins of the invention.

Moreover, the proteins found to bind to the proteins of the invention may themselves be employed, in an analogous fashion to the way in which the proteins of the invention were used as noted above and below, to isolate, identify and characterize other proteins, factors, etc. which are capable of binding to the proteins of the invention-binding proteins and which may represent factors involved further downstream in the associated signaling process, or which may have signaling activities of their and hence would represent proteins involved in a distinct signaling process.

The DNA sequences and the encoded proteins of the invention may be produced by any standard recombinant DNA procedure (see for example, Sambrook, et al., 1989) in which suitable eukaryotic or prokaryotic host cells are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs, fragments and derivatives, and thus the vectors encoding them also include vectors encoding analogs and fragments of these proteins, and the transformed hosts include those producing such analogs and fragments. The derivatives of these proteins are the derivatives produced by standard modification of the proteins or their analogs or fragments, produced by the transformed hosts.

The present invention also relates to pharmaceutical compositions for modulation of the effects mediated by B1. The pharmaceutical compositions comprising, as an active ingredient, any one or more of the following: (i) one or more of the DNA sequences of the invention, or parts of them, subcloned into an appropriate expression vector; (ii) a protein according to the invention, its biologically active fragments, analogs, derivatives or a mixture thereof; (iii) a recombinant animal virus vector encoding for a protein according to the invention, its biologically active fragments, analogs or derivatives.

The pharmaceutical compositions are applied according to the disease to be treated and in amounts beneficial to the patient, depending on body weight and other considerations, as determined by the physician.

As noted above, B1 may possibly be an indirect modulator of TRAF2, and as such it may possibly be involved in NF-κB activation via the TRAF2-NIK-interaction. B1 thus has a possible role in cell survival pathways in ways that TRAF2 functions independently or in conjunction with other proteins (e.g. p55 TNF and p75 TNF receptors, FAS/APO1 receptor, MORT-1, RIP and TRADD). In this respect, there has been recognized the importance to design drugs which may enhance or inhibit the TRAF2-NIK interaction, as desired. For example, when it is desired to increase the cell cytotoxicity induced by TNF it would be desired to inhibit NF-κB induction, by inhibiting the TRAF2-NIK interaction or by inhibiting TRAF2 and/or NIK specifically. Likewise, for example, when it is desired to inhibit the cell cytotoxicity induced by TNF it would be desired to enhance NF-κB induction by enhancing the TRAF2-NIK interaction or by enhancing TRAF2- and/or NIK-specific NF-κB induction. There are many diseases in which such drugs can be of great help. Amongst others, (see above discussion as well) acute hepatitis in which the acute damage to the liver seems to reflect FAS/APO1 receptor-mediated death of the liver cells following induction by the Fas ligand; autoimmune-induced cell death such as the death of the β Langerhans cells of the pancreas, that results in diabetes; the death of cells in graft rejection (e.g., kidney, heart and liver); the death of oligodendrocytes in the brain in multiple sclerosis; and AIDS-inhibited T cell suicide which causes proliferation of the AIDS virus and hence the AIDS disease.

In such cases, it would be desired to inhibit the FAS/APO1 receptor-mediated cell cytotoxicity (apoptosis) pathway and enhance the FAS/APO1 receptor-mediated induction of NF-κB via TRAF2 and the TRAF2-NIK interaction. One way of doing this would be to increase the amount of NIK in the cells or to increase the amount of TRAF2 and NIK so that the NIK- or TRAF2-NIK-mediated induction of NF-κB activation will be increased providing higher levels of NF-κB activation and hence cell survival; or so that the direct or indirect interaction between FAS/APO1 receptor and TRAF2 (or TRAF2-NIK) will be increased resulting in a decrease in FAS/APO1 receptor interactions with cell cytotoxic mediators (e.g MACH, see scheme in FIG. 2) to provide for an increase in the induction of NF-κB activation and cell survival.

Conversely, in the case of, for example, tumors and infected cells (see also discussion above) it would be desired to increase the FAS/APO1 receptor-mediated cell cytotoxicity to bring about increased cell death. In this case it would be desired to inhibit FAS/APO1 receptor-TRAF2 (or -TRAF2-NIK) interactions and/or to inhibit NIK directly, and thereby to decrease the induction of NF-κB activity.

As the B1 protein of the invention may possibly have an interaction with TRAF2, it may be possible to enhance or to block this interaction and thereby to enhance or to inhibit the activity of TRAF2, in particular, the TRAF2-interaction with NIK and the associated induction of NF-κB activation. Enhancement or inhibition of the interaction between B1 and TRAF2 may possibly be direct or via other proteins (e.g. c-IAP1, c-IAP2) which bind to TRAF2 and which possibly interact with B1 directly or indirectly. Thus, by focusing on the B1 protein and modulating its possible interaction (direct or indirect) with TRAF2 it is possible also to modulate the activity of TRAF2 and thereby also the effects of FAS/APO1 (FAS-R) as well as p55-TNF-R as noted above.

As also noted above, B1 may possibly act directly on the mediators of cell death, namely, various caspase enzymes whose proteolytic activity leads to cell death. Accordingly, the above mentioned FAS/APO1 (FAS-R) or p55 TNF-R effects may be modulated directly or indirectly by B1 via B1's possible modulation of the caspases (e.g. MACH and others) which are associated with p55 TNF-R, FAS-R or its binding protein MORT-1 and which apparently effect the apoptotic reactions mediated thereby. Thus if B1 interacts with these caspases in a way that enhances their activity, then such an interaction should be augmented when cell death is desired as noted above, or should be inhibited when cell death is not desired as noted above.

Thus, in view of the above various substances such as peptides, organic compounds, antibodies, etc. may be screened to obtain specific drugs which are capable of inhibiting the possible interaction between B1 and the various other proteins, when such an interaction is not desired. Such drugs are likely to be those which specifically recognize the prodomain (CARD) of B1, for example, peptides, organic molecules, antibodies or antibody fragments, which bind specifically to the B1 CARD and prevent it interacting with other CARD-containing proteins. Conversely, when such an interaction between B1 and the other proteins is desired, then this may be enhanced by increasing the amounts of B1 in the cells by standard procedures noted in (i) above. Here too, it may also be possible to screen for various specific drugs which may be capable of enhancing the activity of B1 intracellularly or of enhancing its interaction with other proteins.

Additionally, as noted above, B1 also has a kinase domain which may be involved in its modulatory effects of inflammation, cell death or survival pathways. Accordingly, this kinase domain may serve to bind and phosphorylate various proteins and thereby increase or decrease their activity and in this way increase or decrease the activity of the inflammation, cell death or cell survival pathways, as the case may be. Accordingly, various peptides, organic compounds, antibodies, etc., may be screened to obtain specific drugs which are capable of inhibiting the kinase activity of B1 when this is desired either for inhibiting or enhancing inflammation, cell death or survival pathways.

A non-limiting example of how peptide inhibitors of the B1 interaction with other proteins via its prodomain or kinase domain, as noted above, would be designed and screened is based on previous studies on peptide inhibitors of ICE or ICE-like proteases, the substrate specificity of ICE and strategies for epitope analysis using peptide synthesis. The minimum requirement for efficient cleavage of a peptide by ICE was found to involve four amino acids to the left of the cleavage site with a strong preference for aspartic acid in the $P_1$ position and with methylamine being sufficient to the right of the $P_1$ position (Sleath et al., 1990; Howard et al., 1991; Thornberry et al., 1992). Furthermore, the fluorogenic substrate peptide (a tetrapeptide), acetyl-Asp-Glu-Val-Asp-α-(4-methyl-coumaryl-7-amide) (SEQ ID NO:3) abbreviated Ac-DEVD-AMC, corresponds to a sequence in poly (ADP-ribose) polymerase (PARP) found to be cleaved in cells shortly after FAS-R stimulation, as well as other apoptotic processes (Kaufmann, 1989; Kaufmann et al., 1993; Lazebnik et al., 1994), and is cleaved effectively by CPP32 (a member of the CED3/ICE protease family) and MACH proteases.

As Asp in the $P_1$ position of the substrate appears to be important, tetrapeptides having Asp as the fourth amino acid residue and various combinations of amino acids in the first three residue positions can be rapidly screened for binding to the active site of the proteases using, for example, the method developed by Geysen (Geysen, 1985; Geysen et al., 1987) where a large number of peptides on solid supports were screened for specific interactions with antibodies. The binding of MACH proteases to specific peptides can be detected by a variety of well known detection methods within the skill of those in the art, such as radiolabeling, etc. This method of Geysen's was shown to be capable of testing at least 4000 peptides each working day.

In a similar way the exact binding region or region of homology which determines the interaction between B1 and other proteins can be elucidated and then peptides may be screened which can serve to block this interaction, e.g. peptides synthesized having a sequence similar to that of the binding region or complementary thereto which can compete with natural B1 for binding to, or otherwise interacting with other proteins of the cell death or cell survival pathways, via the CARD or kinase domains, or even the intermediary domain of B1 between its CARD and kinase domains.

Since it may be advantageous to design peptide inhibitors that selectively inhibit B1 interactions without interfering with physiological cell death or survival processes in which other members of the intracellular signaling pathways are involved, the pool of peptides binding to B1 in an assay such as the one described above can be further synthesized as a fluorogenic substrate peptide to test for selective binding of B1 to such other proteins to select only those specific for B1. Peptides which are determined to be specific for, for example, the CARD or kinase domain of B1, can then be modified to enhance cell permeability and modulate inflammation, cell death or cell survival processes, reversibly or irreversibly. Thornberry et al. (1994) reported that a tetrapeptide (acyloxy) methyl ketone Ac-Tyr-Val-Ala-Asp-$CH_2OC$ (O)-[2,6-$(CF_3)_2$] Ph was a potent inactivator of ICE. Similarly, Milligan et al. (1995) reported that tetrapeptide inhibitors having a chloromethylketone (irreversibly) or aldehyde (reversibly) groups inhibited ICE. In addition, a benzyloxycarboxyl-Asp-$CH_2OC$ (O)-2,6-dichlorobenzene (DCB) was shown to inhibit ICE (Mashima et al., 1995). Accordingly, in an analogous way, tetrapeptides that selectively bind to, for example, the CARD or kinase domain of B1, can be modified with, for example, an aldehyde group, chloromethylketone, (acyloxy) methyl ketone or a $CH_2OC$ (O)-DCB group to create a peptide modulator of B1 activity. Further, to improve permeability, peptides can be, for example, chemically modified or derivatized to enhance their permeability across the cell membrane and facilitate the transport of such peptides through the membrane and into the cytoplasm. Muranishi et al. (1991) reported derivatizing thyrotropin-releasing hormone with lauric acid to form a lipophilic lauroyl derivative with good penetration characteristics across cell membranes. Zacharia et al. (1991) also reported the oxidation of methionine to sulfoxide and the replacement of the peptide bond with its ketomethylene isoester ($COCH_2$) to facilitate transport of peptides through the cell membrane. These are just some of the known modifications and derivatives that are well within the skill of those in the art.

Furthermore, drug or peptide inhibitors, which are capable of inhibiting the activity of, for example, the cell death or cell survival pathways by interfering with the possible interaction between B1 and any of the proteins it binds to via the CARD, kinase or intermediate domains, can be conjugated or complexed with molecules that facilitate entry into the cell.

U.S. Pat. No. 5,149,782 discloses conjugating a molecule to be transported across the cell membrane with a membrane blending agent such as fusogenic polypeptides, ion-channel forming polypeptides, other membrane polypeptides, and long chain fatty acids, e.g. myristic acid, palmitic acid. These membrane blending agents insert the molecular conjugates into the lipid bilayer of cellular membranes and facilitate their entry into the cytoplasm.

Low et al., U.S. Pat. No. 5,108,921, reviews available methods for transmembrane delivery of molecules such as, but not limited to, proteins and nucleic acids by the mechanism of receptor mediated endocytotic activity. These receptor systems include those recognizing galactose, mannose, mannose 6-phosphate, transferrin, asialoglycoprotein, transcobalamin (vitamin $B_{12}$), $\alpha$-2 macroglobulins, insulin and other peptide growth factors such as epidermal growth factor (EGF). Low et al. teaches that nutrient receptors, such as receptors for biotin and folate, can be advantageously used to enhance transport across the cell membrane due to the location and multiplicity of biotin and folate receptors on the membrane surfaces of most cells and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

ICE is known to have the ability to tolerate liberal substitutions in the $P_2$ position and this tolerance to liberal substitutions was exploited to develop a potent and highly selective affinity label containing a biotin tag (Thornberry et al., 1994). Consequently, the $P_2$ position as well as possibly the N-terminus of the tetrapeptide inhibitor can be modified or derivatized, such as to with the addition of a biotin molecule, to enhance the permeability of these peptide inhibitors across the cell membrane.

In addition, it is known in the art that fusing a desired peptide sequence with a leader/signal peptide sequence to create a "chimeric peptide" will enable such a "chimeric peptide" to be transported across the cell membrane into the cytoplasm.

As will be appreciated by those of skill in the art of peptides, the peptide inhibitors of the B1 interaction with other proteins, as noted above, according to the present invention is meant to include peptidomimetic drugs or inhibitors, which can also be rapidly screened for binding to the CARD, kinase or intermediate domain of B1 to design perhaps more stable inhibitors.

It will also be appreciated that the same means for facilitating or enhancing the transport of peptide inhibitors across cell membranes as discussed above are also applicable to the analogs, fragments or isoforms of B1, as well as other B1-specific peptides and proteins (including fusion proteins) which exert their effects intracellularly.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, Nature, 256:495-497 (1975); U.S. Pat. No. 4,376,110; Ausubel et al., eds., Harlow and Lane ANTIBODIES: A LABORATORY MANUAL, Cold Spring Harbor Laboratory (1988); and Colligan et al., eds., Current Protocols in Immunology, Greene Publishing Assoc. and Wiley Interscience N.Y., (1992-1996), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules of which different portions are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. NatL Acad. Sci. USA* 81:3273-3277 (1984); Morrison et al., *Proc. Natl Acad. Sci. USA* 81:6851-6855 (1984); Boulianne et al., *Nature* 312:643-646 (1984); Cabilly et al., European Patent Application 125023 (published Nov. 14, 1984); Neuberger et al., *Nature* 314:268-270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J Immunol* 137:1066-1074 (1986); Robinson et al., International Patent Application No. WO8702671 (published May 7, 1987); Liu et al., *Proc. Natl. Acad. Sci USA* 84:3439-3443 (1987); Sun et al., *Proc. Natl. Acad. Sci USA* 84:214-218 (1987); Better et al., *Science* 240:1041-1043 (1988); and Harlow and Lane, ANTIBODIES: A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the B1 proteins, analogs, fragments or derivatives thereof, of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above B1 protein, or analogs, fragments and derivatives thereof.

The anti-Id mAbs thus have their own idiotypic epitopes, or "idiotopes" structurally similar to the epitope being evaluated, such as GRB protein-a.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J Nucl. Med.* 24:316-325 (1983)).

It will be appreciated that Fab and F(ab')2 and other fragments of the antibodies useful in the present invention may be used for the detection and quantitation of the B1 protein according to the methods disclosed herein for intact antibody molecules. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the B1 protein in a sample or to detect presence of cells which express the B1 protein of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of the B1 protein of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the B1 protein, but also its distribution on the examined tissue. Using the present invention, those of ordinary skill will readily perceive that any of wide variety of histological methods (such as staining procedures) can be modified in order to achieve such in situ detection.

Such assays for the B1 protein of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the B1 protein, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support", "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and used in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholin-esterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactive labeling the antibodies or antibody fragments, it is possible to detect R-PTPase through the use of a radioimmunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a γ-counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}E$, or others of the lanthanide series. These metals can be attached to the antibody using such metal chelating groups as diethylenetriamine pentaacetic acid (ETPA).

The antibody can also be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an immunometric assay, also known as a "two-site" or "sandwich" assay. In a typical immunometric assay, a quantity of unlabeled antibody (or fragment of antibody) is bound to a solid support or carrier and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

As mentioned above, the present invention also relates to pharmaceutical compositions comprising recombinant animal virus vectors encoding the B1 proteins, which vector also encodes a virus surface protein capable of binding specific target cell (e.g., cancer cells) surface proteins to direct the insertion of the B1 protein sequences into the cells. Further pharmaceutical compositions of the invention comprises as the active ingredient (a) an oligonucleotide sequence which is an anti-sense sequence of the B1 protein sequence, or (b) drugs that block the B1 interaction with other proteins.

Pharmaceutical compositions according to the present invention include a sufficient amount of the active ingredient to achieve its intended purpose. In addition, the pharmaceutical compositions may contain suitable pharmaceutically acceptable carriers comprising excipients and auxiliaries which facilitate processing of the active compounds into preparations which can be used pharmaceutically and which can stabilize such preparations for administration to the subject in need thereof as are well known to those of skill in the art.

The B1 protein and its isoforms or isotypes are suspected to possibly be expressed in different tissues at markedly different levels and apparently also with different patterns of isotypes in an analogous fashion to the expression of various other proteins involved in the intracellular signaling pathways as indicated in the above listed co-owned co-pending patent applications. These differences may possibly contribute to the tissue-specific features of response to the Fas/APO1-ligand and TNF. As in the case of other CED3/ICE homologs (Wang et al., 1994; Alnemri et al., 1995), the present inventors have previously shown (in the above mentioned patent applications) that MACH isoforms that contain incomplete CED3/ICE regions (e.g., MACHα3) are found to have an inhibitory effect on the activity of co-expressed MACHα1 or MACHα2 molecules; they are also found to block death induction by Fas/APO1 and p55-R (p55-TNF-R). Expression of such inhibitory isoforms in cells may constitute a mechanism of cellular self-protection against Fas/APO1- and TNF-mediated cytotoxicity. The wide heterogeneity of MACH isoforms, which greatly exceeds that observed for any of the other proteases of the CED3/ICE family, should allow a particularly fine tuning of the function of the active MACH isoforms. It is also known that BCL2, BCL-$X_L$ and other members of the BCL2 family are expressed and are active to varying degrees in different types of cells giving rise to variations in the susceptibility of different cells to induced apoptosis, i.e. some cells are more likely to survive than others (see above noted review by Yang and Korsmeyer, 1996).

As noted above, the B1 proteins or possible isoforms may possibly have varying effects in different tissues. For example, such varying effects may possibly be as regards their interaction with other proteins of the inflammation, cell death or cell survival processes and their influence thereby on the activity of these pathways, in particular the balance between them and whether or not this balance will be shifted one way or the other.

It is also possible that some of the possible B1 protein isoforms serve other functions. For example, B1, its analogs, or isoforms may also act as docking sites for molecules that are involved in other intracellular pathways not related to the above noted cell death or survival pathways.

Due to the unique ability of Fas/APO1 and TNF receptors to cause cell death, as well as the ability of the TNF receptors to trigger other tissue-damaging activities, aberrations in the function of these receptors could be particularly deleterious to the organism. Indeed, both excessive and deficient functioning of these receptors have been shown to contribute to pathological manifestations of various diseases (Vassalli, 1992; Nagata and Golstein, 1995). Identifying the molecules that participate in the signaling activity of the receptors, and finding ways to modulate the activity of these molecules, could direct new therapeutic approaches. In view of the suspected important role of the TRAF proteins, and hence the B1 protein which may possibly interact directly or indirectly therewith, or the suspected interaction between B1 and various caspases, it seems particularly important to design drugs that can influence or modulate the interaction between B1 and these other proteins with which it interacts, and in this way to enhance or inhibit cell death or cell survival as is desired.

The present invention also concerns proteins or other ligands which can bind to the B1 proteins of the invention and thereby modulate/mediate the activity of the B1 proteins. Such proteins or ligands may be screened, isolated and produced by any of the above mentioned methods. For example, there may be isolated a number of new ligands, including proteins, capable of binding to the B1 proteins of the invention.

As detailed above, such new B1-binding proteins/ligands, may serve as, for example, inhibitors or enhancers of B1-mediated activity, and as such will have important roles in various pathological and other situations as detailed above. Another function of such B1-binding proteins/ligands would be to serve as specific agents for the purification of the B1 proteins by, for example, affinity chromatography, these new binding proteins/ligands being attached to the suitable chromatography matrices to form the solid or affinity support/matrix through which a solution, extract or the like, containing the B1 proteins, will be passed and in this way to facilitate the purification thereof. Such methods of affinity chromatography are now well known and generally standard procedures of the art.

Likewise, all of the above mentioned B1 proteins, analogs, fragments, isoforms and derivatives of the present invention may be used to purify by affinity chromatography the various proteins of the inflammation, cell death or survival pathways to which they bind. For example, B1 proteins and analogs, fragments and muteins thereof may be used for the affinity chromatography purification of B1-binding proteins. Such a method for identifying and producing these B1-binding proteins, will include a screening step in which the B1 protein, or at least a specific portion thereof, is used as a substrate or 'bait' to obtain proteins or any other ligand capable of binding thereto; followed by steps of identifying and characterizing such proteins/ligands so-obtained; and subsequently producing such proteins/ligands in substantially isolated and purified forms. All these steps are well known to those of skill in the art and are detailed herein above and herein below.

The invention will now be described in more detail in the following non-limiting examples and the accompanying drawings:

It should also be noted that the procedures of:

i) two-hybrid screen and two-hybrid β-galactosidase expression test; (ii) induced expression, metabolic labeling and immunoprecipitation of proteins; (iii) in vitro binding; (iv) assessment of the cytotoxicity; and (v) Northern and sequence analyses, as well as other procedures used in the following Examples have been detailed in previous publications by the present inventors in respect of other intracellular signaling proteins and pathways (see, for example, Boldin et al., 1995a, 1995b, and Boldin et al. 1996). These procedures also appear in detail in the co-owned co-pending Israel Application Nos. 114615, 114986, 115319, 116588, 117932, and 120367 as well as the corresponding PCT application No. PCT/US96/10521). Accordingly, the full disclosures of all these publications and patent applications are included herein in their entirety and at least as far as the detailed experimental procedures are concerned. As regards the NIK protein and its role in activating NF-κB and hence cell survival and the role played by TRAF2 in this cell survival pathway, for example the interaction between TRAF2 and p55-R, FAS-R, RIP and other proteins, these have been detailed by the present inventors in the above noted co-owned, co-pending IL and PCT applications and in Malinin et al., 1997.

EXAMPLE 1

Isolation, Sequencing and Partial Characterization of the New B1 Protein

Employing various methods as described in the co-owned patent applications mentioned above, a new cloned DNA sequence has been isolated, sequenced and partially characterized. This DNA sequence encodes a new protein, originally designated as a c-IAP binding kinase (CBK) by virtue of its homology to c-IAP proteins and of its having a kinase domain, but now is designated as B1.

Briefly, in order to further elucidate the intracellular activity of the recently discovered cellular inhibitors of apoptosis (IAP) homologs c-IAP1 and c-IAP2 (see Rothe et al., 1995; Uren et al., 1996; Hofmann et al., 1997) and with which intracellular proteins they interact, the c-IAP sequences were used to screen for other possibly homologous, or otherwise related sequences in various databases, including those having uncharacterized (and not fully sequenced) expressed sequence tags (ests). In this way a partial sequence of a new clone was found that had high homology to c-IAP1. Using this partial sequence, which had previously not been characterized in any way, PCR primers were prepared for the PCR cloning of the full-length DNA sequence of this new clone using, as template DNA; cDNA libraries commercially obtained.

As a result, a new full-length DNA clone was obtained encoding a heretofore unknown protein, namely, the new protein designated B1. A sequence was initially determined for B1 (DNA and amino acid). A further analysis and determination of the initial B1 sequence revealed some differences at the N-terminal part of the amino acid sequence (the 5' end of the nucleotide sequence), which involved the first 19 deduced amino acid residues. This further sequence determination and analysis yielded the deduced B1 amino acid sequence and the nucleotide sequence coding therefore as shown in FIGS. 3A and B, respectively.

Upon analysis of the amino acid sequences of FIG. 3, it arises that there is a kinase motif at the N-terminal end of the protein which is encoded by the first approximately 1000 nucleotides of the open reading frame (ORF) of the nucleotide sequences of FIG. 3. Further, towards the C-terminal end of the amino acid sequence there is a prodomain (CARD) structure which is common to a number of intracellular proteins involved in apoptotic signaling pathways, for example, c-IAP1, RAIDD (see Duan and Dixit, 1997), and other caspases such as ICE and ICH-1. In the amino acid sequence of B1 depicted in FIG. 3A there is shown the N-terminal kinase domain (boxed region) and the C-terminal CARD (underlined region). Between these two domains is the intermediatory domain of the B1 protein.

The above noted kinase domain of B1 has high homology (or similarity) to the known RAF-type kinases and the RIP-kinase domain.

The above mentioned prodomain of B1 has recently also been designated as CARD for 'caspase recruitment domain' (see Hofmann et al., 1997) and appears to serve as a region through which various proteins interact during the apoptotic signaling process intracellularly. For example, the p55 TNF-R which does not have a prodomain (or CARD) interacts with another intracellular protein TRADD (an adaptor protein) via the death domain region present on both these proteins. In turn, TRADD can interact with RIP and with RAIDD (additional such adaptor proteins, see also Hofmann et al., 1997; Duan and Dixit, 1997; Wallach, 1997) all of which have death domains, such that, via the death domain region the p55-TNF-R can be complexed directly or indirectly to RAIDD. RAIDD has a prodomain (or CARD) which can interact or bind with one or more caspases, e.g. ICH-1 (caspase-2), and possibly others, and thereby can link the p55-TNF-R to such caspases and bring about apoptosis via the action of the caspases. Likewise, the p75-TNF-R can interact with the TRAF2 and TRAF1 proteins via common motifs, and the TRAF proteins can interact with c-IAP1 and c-IAP2. In a similar fashion (see also Malinin et al., 1997, WO 97/37016), by virtue of the ability of the FAS-R (Fas/APO1) to be able to interact with MORT1 (FADD), which, in turn, interacts with TRADD (all via their common death domains), and the ability of TRADD to interact with TRAF2, MORT1 can thus be so linked to c-IAP1, c-IAP2 (via TRAF2) and thereby to ICE, Mch6 and other caspases, or be so linked to ICH-1, FLICE/MACH or other caspases (via the TRADD-RIP-RAIDD interactions, noted above). It should also be noted that the p55 TNF-R can also be so linked to ICE, Mch6 and other such caspases via the above noted TRADD-TRAF2-cIAP1, c-IAP2-ICE, Mch6 interactions, this by virtue of the ability of p55 TNF-R to interact with TRADD as well.

In addition, it is known that TRAF2 is also involved in an intracellular pathway (or more than one pathway) that promotes cell survival via the induction of NF-κB activation. In this pathway(s) NIK appears to be directly involved in the phosphorylation of I-κB that leads to I-κB dissociation from NF-κB and thereby activation of NF-κB, whereby NF-κB can enter the nucleus and initiate transcription of various genes, the expression of which are linked to cell survival (see also 'Background' section above).

Thus, TRAF2 is involved in both the cell death and cell survival pathways and depending on which proteins predominantly interact with TRAF2 at any given period in response to various external stimuli (e.g. ligands bind the various receptors), the cell may undergo cell death or cell survival induction. Clearly, there is a fine balance between the various intracellular signaling proteins that can be shifted to either of the opposing cell death or cell survival pathways, and TRAF2 appears to be one of the key proteins maintaining this balance and being responsible for any shift in the balance one way or the other.

Figure 2:
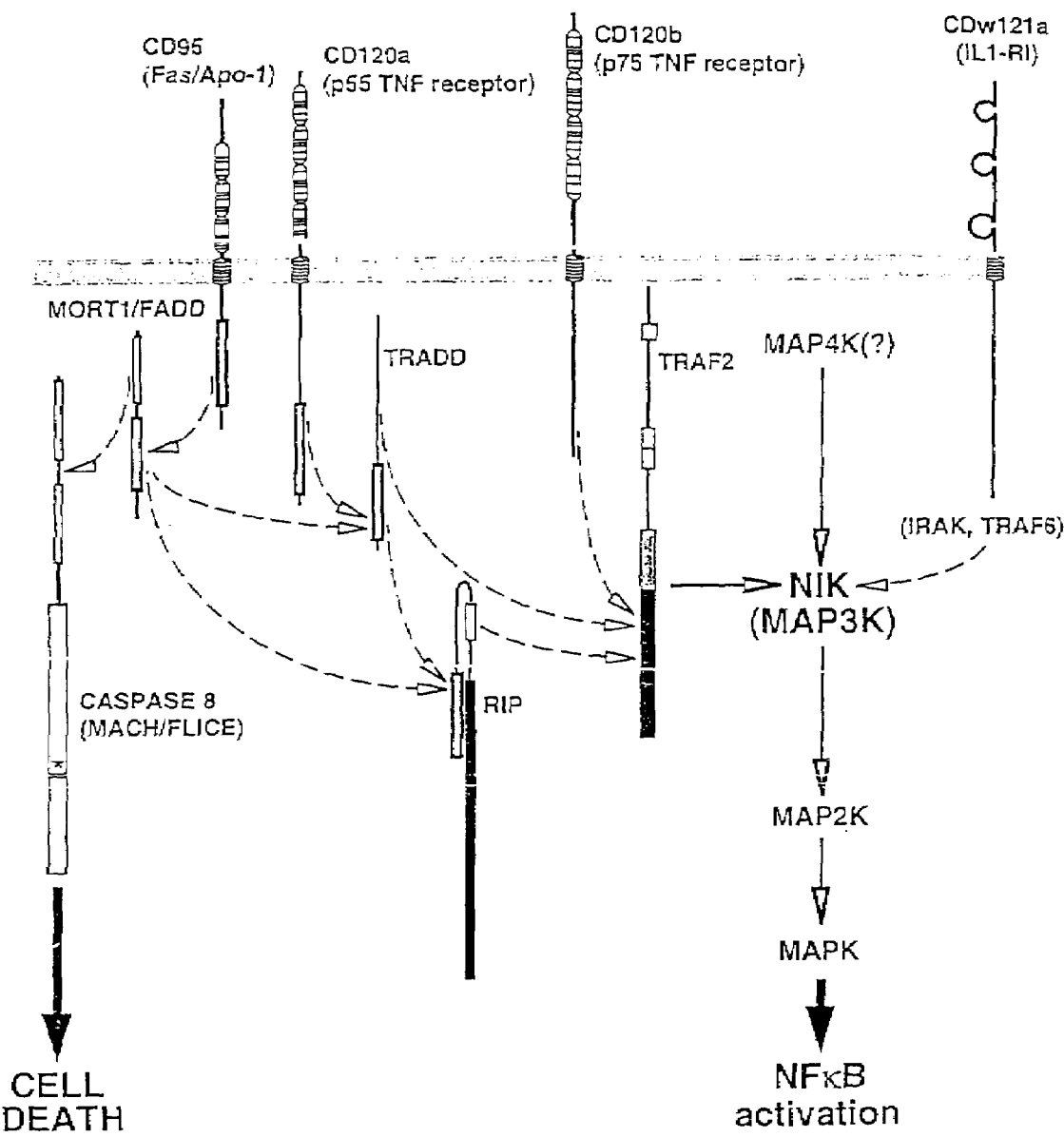
FIG. 2 shows a schematic diagram illustrating some of the proteins involved in inflammation, cell death and cell survival (NF-kB activation) pathways.

In FIG. 1 there is shown schematically the structure of the TRAF2 protein with its various domains and in FIG. 2 there is shown schematically some of the possible interactions between various cellular receptors and intracellular signaling proteins and their involvement in cell death or cell survival (NF-κB activation) pathways.

Accordingly, the possibility arises that the new B1 protein of the present invention may have an important modulatory role in the inflammation, cell death and cell survival pathways. B1 has a prodomain (or CARD domain) which may possibly interact even indirectly with the prodomain of c-IAP1, c-IAP2, RAIDD and various caspases (ICE, ICH-1, etc.) and thereby it may possibly interact even indirectly with TRAF2 and the various proteins which interact directly or indirectly with TRAF2, including RIP, TRADD, p75 TNF-R, p55 TNF-R, MORT-1 and FAS-R. B1 also has a kinase domain and as such it may possibly be involved directly or indirectly in the MAP kinase pathway, of which NIK appears to be a member, and thereby may also be involved in the NF-κB activation pathway.

Moreover, B1 by virtue of its homology to c-IAP1, may possibly be a modulator of c-IAP1 (and c-IAP2) activity by modulating c-IAP1's biological activity or by modulating the binding of c-IAP1 to other proteins. In this regard (see also Example 2 below), B1 may possibly act to increase apoptosis by interacting even indirectly with c-IAP proteins (c-IAP1, c-IAP2) and disrupting or otherwise decreasing their ability to recruit caspases and restrict their proteolytic activity, with the result that more caspases will be free to act proteolytically.

Another possibility is that B1 via its above-mentioned possible ability to be able to interact with various mediators of cell death, directly or indirectly, including TRAF-1 and TRAF2, RAIDD, RIP, TRADD, p55-TNF-R, p75-TNF-R, MORT-1 and FAS-R; and with various caspases, may possibly serve to link these proteins to the caspases and thereby possibly serve as an intermediary agent in the cell death pathway(s) to which these proteins belong. As such, B1 may be an important mediator of apoptosis.

A further possibility is that by the possible interaction (even indirect) of B1 with c-IAP proteins noted above, B1 may possibly prevent c-IAP binding or interaction with TRAF2 and thereby may possibly block TRAF2 activity with respect to the MAP kinase pathway, for example, TRAF2-c-IAP interactions may be important for TRAF2 interactions with NIK, and if this is prevented by B1 interaction with c-IAP, then TRAF2-mediated NF-κB activation may be blocked resulting in less enhancement of cell survival and possibly an increase in cell death.

A still further possibility is that B1 may act in a more direct manner in modulating the activity of the various caspases. Thus via interactions, direct or indirect, between the prodomains (CARD domains) of B1 and various caspases, B1 may possibly lead to an increase in the activity of these enzymes and thereby increase the cytotoxicity of these enzymes. In this way B1 may be a direct augmentor of apoptosis by recruiting or otherwise activating caspases, (see also Example 2 below).

An additional possibility is that B1 may act to modulate intracellular signaling pathways mediating cell death or cell survival by binding to or interacting with other as yet unknown proteins.

It is interesting to note (see above) that B1 has a kinase domain similar to the RIP-kinase. RIP is also a central protein involved in the balance between the cell death and cell survival pathways by virtue of its ability to link between the cell death mediators (e.g. p55 TNF-R, FAS-R, MORT-1, TRADD) and TRAF-2 and thereby to NF-κB activation and cell survival (see FIG. 2). The RIP-kinase activity may also be a factor in this fine balance, depending on what are the substrates for this kinase, for example, what proteins are phosphorylated by RIP and whether this influences their activity towards increase apoptopic activity; decreased apoptopic activity, increased NF-K-R activation or decreased NF-κ activation. By analogy, B1 may possibly also play such a central role in which the kinase activity thereof may be important depending on which proteins are substrates for such kinase activity.

EXAMPLE 2

Analysis of the Biological Activity of B1 Protein (i) Preliminary Binding Assay to Determine which Known Proteins can Bind to B1

Using the methods from WO 97/37016 methods to prepare and express DNA constructs and the yeast two-hybrid binding assay, a construct of B1 from which was removed its kinase domain, i.e. a truncated B1 having only the intermediate region and the C-terminal CARD region, was employed to test for its ability to bind various known proteins involved in intracellular signaling pathways (cell death and survival pathways). The initial, preliminary results (not shown) seem to indicate that this truncated B1 binds to BCL2.

(ii) Cell Cytotoxicity Analysis to Determine the Effect of B1 on Cell Death or Cell Survival Using the methods from WO 97/37016 methods for preparing DNA constructs and transfecting/transforming cells therewith and determining the effect on cell death or cell survival by the expressed products of these constructs, a DNA construct encoding the full-length B1 protein was used to transfect cells in culture. Further, in another set of experiments the B1-encoding construct was used to co-transfect cells with other constructs encoding FAS-R, p55 TNF-R and RIP, amongst others.

The results obtained from these transfections (not shown) indicate that the expressed B1 protein on its own does not cause cell death. However, when B1 is expressed together with FAS-R, p55 TNF-R or RIP, it enhances the level of cell death induced by these known inducers of cell death.

These results taken with those of (i) above, that B1 may bind to BCL2, raise the possibility that B1 may serve as an inhibitor of BCL2 activity, i.e. that B1 may prevent BCL2's activity towards protecting cells against apoptosis (see 'Background' section above), and as such B1 apparently is capable of enhancing the cell death pathways induced by FAS-R, p55 TNF-R and RIP, and possibly other inducers of cell death (as also noted above in "Background" section). In this respect, B1 may possibly act in an analogous way to the BAD protein, a member of the BCL2 family, which binds to BCL2 and BCL-$X_L$ and thereby results in increased levels of BAX and BAK which are known to be directly involved in causing cell death. Another possibility may be that B1, by virtue of its kinase domain, may phosphorylate BCL2 at the phosphorylation sites present on BCL2 and in this way may effect BCL2's activity toward protecting cells against apoptosis, resulting, ultimately, in the observed effect that B1 has on enhancing induced cell death.

Moreover, it is also possible that B1 may, in addition to or independent of its possible interaction with BCL2, effect the induction of NF-κB activation and this via B1's kinase activity acting in the pathway leading to NF-κB activation, for example, B1 may possibly interact with NIK or other kinases in the pathway that NIK is a member, or it may act on other adaptor proteins related thereto, e.g. TRAF2, in such a way as to lead to reduced NF-κB activation, and ultimately reduced cell survival and increased cell death.

Therefore, in summary, it appears that B1 plays a role in the modulation of intracellular signaling pathways whether they are those leading to inflammation, cell death or cell survival. B1 may thus be considered as a 'modulator of intracellular signaling', as it clearly has the ability to influence inflammation, cell death and cell survival pathways in a number of ways be they direct (recruitment of various proteins and activation or inhibition thereof or via kinase activity) or be they indirect (via interaction with various other intermediates, e.g. BCL2, and possibly also c-IAP and thereby to TRAF2, etc; or RAIDD and thereby to RIP, TRADD, etc.).

EXAMPLE 3

Additional Analysis of B1 Biological Activity

NF-κB activity, cell death assay, Northern analysis and INK activity assays were carried out with the following B1 and B1 mutant constructs (see FIG. 6)

B1 (see example 1)

B1 mut, a mutant of B1 in which the lysine at position 47 was replaced with alanine ΔCARD, B1 lacking the CARD domain created by PCR and cloning into expression vectors ΔXba, B1 lacking the CARD domain but shorter at its 3' end than ΔCARD, created by the use of the restriction site and cloning into expression vectors ΔBam, similar to ΔXba and created in the same manner, using the Bam restriction enzyme, ΔNde, containing part of the kinase domain and the CARD domain, created by PCR and cloning into an expression vector, and ΔK, created by PCR using the following primers
1. 5'-CAGAATTCCAGAGTGTTTCAAGTGCCATTC (SEQ ID NO:4);
2. 5'-AACTCGAGACTTACATGCTTTTATTTTGAA (SEQ ID NO:5).

The PCR fragment was cloned into expression vectors and verified by sequencing.

NF-κB activation measurements were carried out by reporter gene assay as described in WO 97/37016. Briefly, cells were co-transfected with the HIV LTR-luciferase gene plasmid (1 µg) and the B1 and B1 mutant expression vectors (3 µg). The amount of transfected DNA was kept constant by addition of an "empty" vector. 24 hours after transfection, the cells were washed with PBS and lysed. Luciferase assay was performed as described in Current Protocols in Molecular Biology, Ausubel et al. The results can be seen in FIG. 6.

Figure 5:
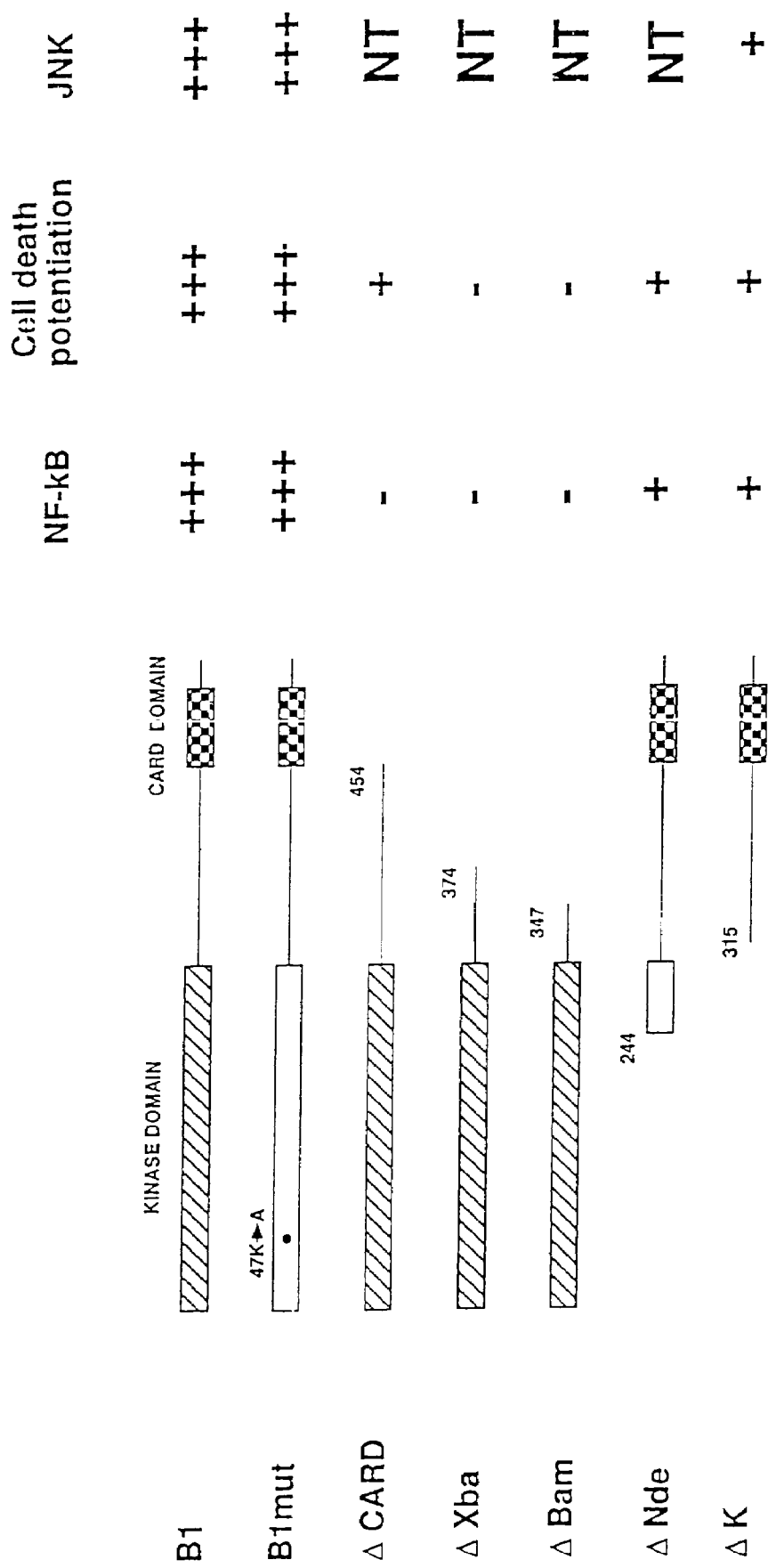
FIG. 5 shows schematically the different B1 constructs tested for NF-κB activity, cell death potentiation and JNK activation.

Cell death assay was carried out by growing 293-T cells in Dulbecco's modified Eagle's minimal essential medium supplemented with 10% fetal calf serum, non-essential amino acids, 100 U/ml penicillin and 100 µg/ml streptomycin. 293-T cells ($5 \times 10^5$ cells in 6 cm dishes) were transiently transfected using the calcium phosphate precipitation method with the cDNAs of the different constructs together with the β-galactosidase expression vector. In the experiments, the results of which are shown in FIG. 5, each dish was transfected with 1 µg of a p55 TNF-R, RIP or TRADD construct, 1 µg of the respective B1 or B1 mutant construct (or, as control, an empty vector), and 1 µg of pSV-β-gal (Promega). The extent of cell death at the end of the incubation period was assessed by determination of β-galactosidase expression, as described by Boldin et al., 1996.

Figure 4:
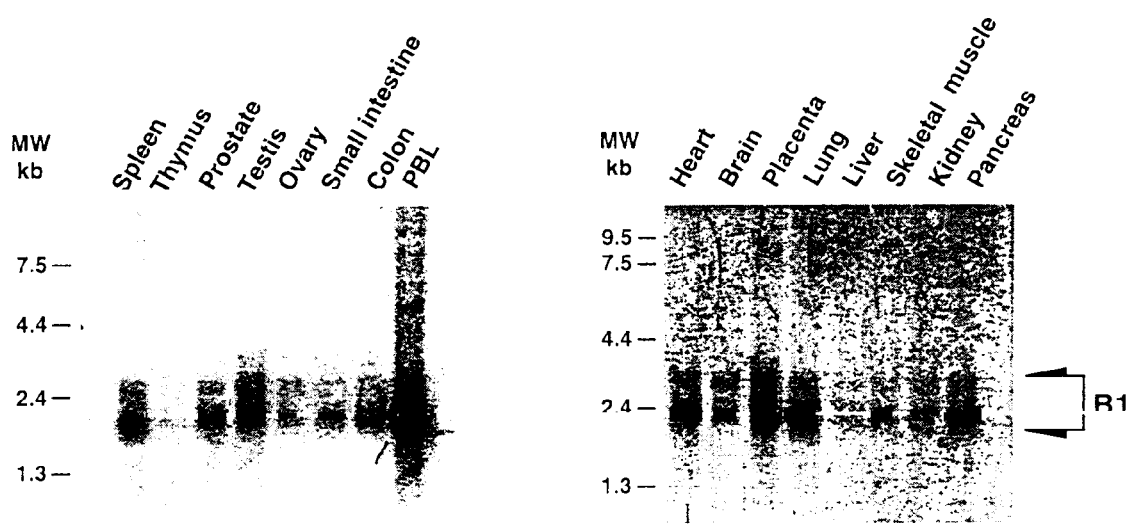
FIG. 4 shows a Northern analysis of B1 expression in different human tissues, which shows that B1 is expressed in most human tissue types.

Northern analysis was performed by conventional methods, see e.g. Boldin et al., 1995, and revealed that B1 is present in many human tissues (FIG. 4).

Figure 7:
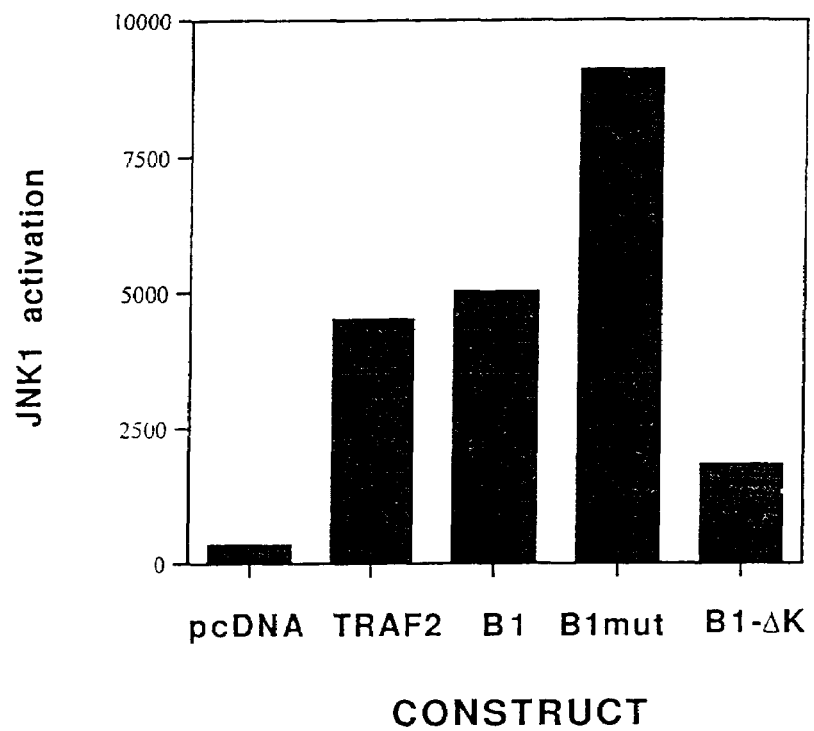
FIG. 7 shows the JNK1 activation results of measurements carried out with some of the above constructs.

JNK activation was carried out by transiently transfecting 293-T cells ($5 \times 10^5$ cells in 6 cm dishes), using the calcium phosphate precipitation method with 1.5 µg of pSR-HA-JNK1 construct (an HA epitope tagged JNK-1 expression vector) and 4 µg each of B1 and B1 mutant construct expression vector. After 24 hrs cells were lysed in lysis buffer (20 mM Hepes pH 7.6, 10 mM EGTA, 40 mM β-glycerophosphate, 2.5 mM MgCl$_2$, 1 mM DTT and 1% NP-40) and Ha-JNK1 protein was immunoprecipitated with anti-HA antibodies (see e.g. Rothe et al., 1995b). (clone 12 CA5). The kinase assay was performed in 30 µl of kinase buffer (20 mM Hepes pH 7.6, 40 mM β-glycerophosphate, 2.0 mM MgCl$_2$, 2 mM DTT, 3 nmole ATP and 3 µCi of γ-P$^{32}$-ATP) at 30° C. for 20 min. Bacterially produced GST-Jun protein (about 10 µg) was used as substrate. The reaction was stopped by addition of 2×SDS-loading buffer, boiled for 3 min and analyzed by SDS-PAGE gel. The results are shown in FIG. 7.

The results in FIG. 6 show that B1 can induce NF-κB activation directly. However, seeing that B1 must also induce NF-κB, this activation appears to be independent of its kinase domain, and it is assumed that it may be connected to the CARD domain, with or without contribution by part or all of the intermediate domain of B1.

Further cell cytotoxicity analysis shows that not only B1 (see example 2 (ii)), but also B1 mut, when expressed together with p55-TNF-R, RIP or TRADD potentiates the level of cell death. ΔCARD, ΔNde and ΔK do so to a lesser extent, while the other constructs do not. This seems to indicate that at least the CARD domain is involved in the potentiation of cell death, possibly together with the intermediate domain.

The results for the JNK activation also seem to indicate that at least the CARD domain is involved in this activation, again possibly together with the intermediate domain.

In addition to the above, tests carried out have shown that B1 autophosphorylates. This is proof that B1 is indeed a kinase.

Furthermore, it has been confirmed that B1 has homology to RIP. Computer analysis indicates a 37% identity of the two proteins on the amino acid level and a homology of 47%. RIP is now widely considered to be mainly an NF-κB modulator and the above results indicate that B1 acts similarly.

EXAMPLE 4

Binding Characteristics

The binding characteristics of B1, and mutants thereof are shown in the following Table VI:

TABLE VI

| DNA-binding hybrid | Activation hybrid | LacZ |
|---|---|---|
| B1 | B1 | +++ |
| B1 | ΔK | +++ |
| ΔK | B1 | +++ |
| ΔK | ΔK | +++ |
| B1 | TRAF2 | − |
| B1 | TRAF3 | − |
| B1 | TRAF6 | − |
| TRAF2 | B1 | − |
| TRAF6 | B1 | − |
| TRAF1 | B1 | + |
| B1 | TANK | − |
| B1 | NIK | − |
| NIK | B1 | − |
| B1 | CASH | − |
| CASH | B1 | − |
| B1 | RIP | − |
| B1 | RAIDD | − |
| B1 | ICE | − |
| B1 | ICH-1 | − |
| B1 | MACHα1(C360S) | − |
| B1 | MORT-1 | − |
| B1 | cIAP-1 | − |
| cIAP-1 | B1 | + |
| RIP | B1 | − |
| RAIDD | B1 | − |
| ICE | B1 | − |
| ICH-1 | B1 | − |
| MACHα1(C360S | B1 | − |

From the results shown in the above table it appear that when B1 functions to induce NF-κB activation, it may do so independently of binding to other proteins known to be involved in NF-κB activation, such as e.g. IRAK, TRAF2, NIK, TRAF6 and RIP. Thus B1 may induce NF-κB activation directly or indirectly via interaction with some other proteins forming part of this activation pathway.

As far as B1's observed cell death enhancing activities are concerned, it also appears from the above table, that B1 does so without direct interaction with various cell death mediators, such as e.g. p55 TNF-R, Fas-R, MORT1, TRADD, RIP, ICE, ICH-1, and the like.

Hence, B1 may also function to enhance cell death by an indirect interaction with these various cell death mediators/modulators or via other proteins.

In view of B1's involvement in both, NF-κB activation, as well as in cell death enhancement, B1 may be a central protein involved in the fine balance between the intracellular pathways leading to cell death or cell survival. In this respect B1, depending on with which protein it interacts, may be capable of shifting the balance between cell death and cell survival.

293 human embryonic kidney cells ($5 \times 10^6$; $2.5 \times 10^6$/per 10 cm dish) were transiently transfected by the calcium phosphate procedure with 10 µg of plasmid encoding HA-tagged B1 protein (HA-B1) and 10 µg of either a plasmid encoding Flag-tagged B1 protein (FL-B1) or one encoding Flag-tagged c-IAP-1 protein (FL-IAP1), or one encoding Flag-tagged TRAF1 (FL-TRAF1), or one encoding Flag-tagged TRAF2 (FL-TRAF2) or with 10 µg of the combination (in 1:1 ratio) of Flag-tagged TRAF1 and non-tagged TRAF2 (FL-TR1+TR2), or with 10 µg of combination (1:1:1) of Flag-tagged TRAF1, non-tagged TRAF2 and c-IAP-1 (FL-TR1+TR2+IAP1). Seven hours after transfection cells were washed and 18 hours later cells were lysed in a buffer containing 50 mM HEPES pH 7.5, 250 mM NaCl, 0.2% NP-40, 5 mM EDTA, 1 mM phenylmethylsulfonyl fluoride, 2.0 µg/ml aprotinin and 20 µg/ml leupeptin (lysis buffer). Immunoprecipitation was performed by incubation (2 h, 4° C.) of 1 ml aliquots of lysate with anti-FLAG epitope antibody (5 µg/aliquot) and with protein G-agarose beads (30 µl/aliquot). Immunoprecipitates were washed three times with lysis buffer and once with PBS, fractionated by 10% SDS-PAGE and transferred to a nitrocellulose membrane (Schleicher & Schuell, Dassel, Germany). Western blot analysis was performed with anti-HA epitope monoclonal antibodies applied at a dilution of 1:1000, and the ECL kit (Amersham, Buckinghamshire, England).

Figure 8:
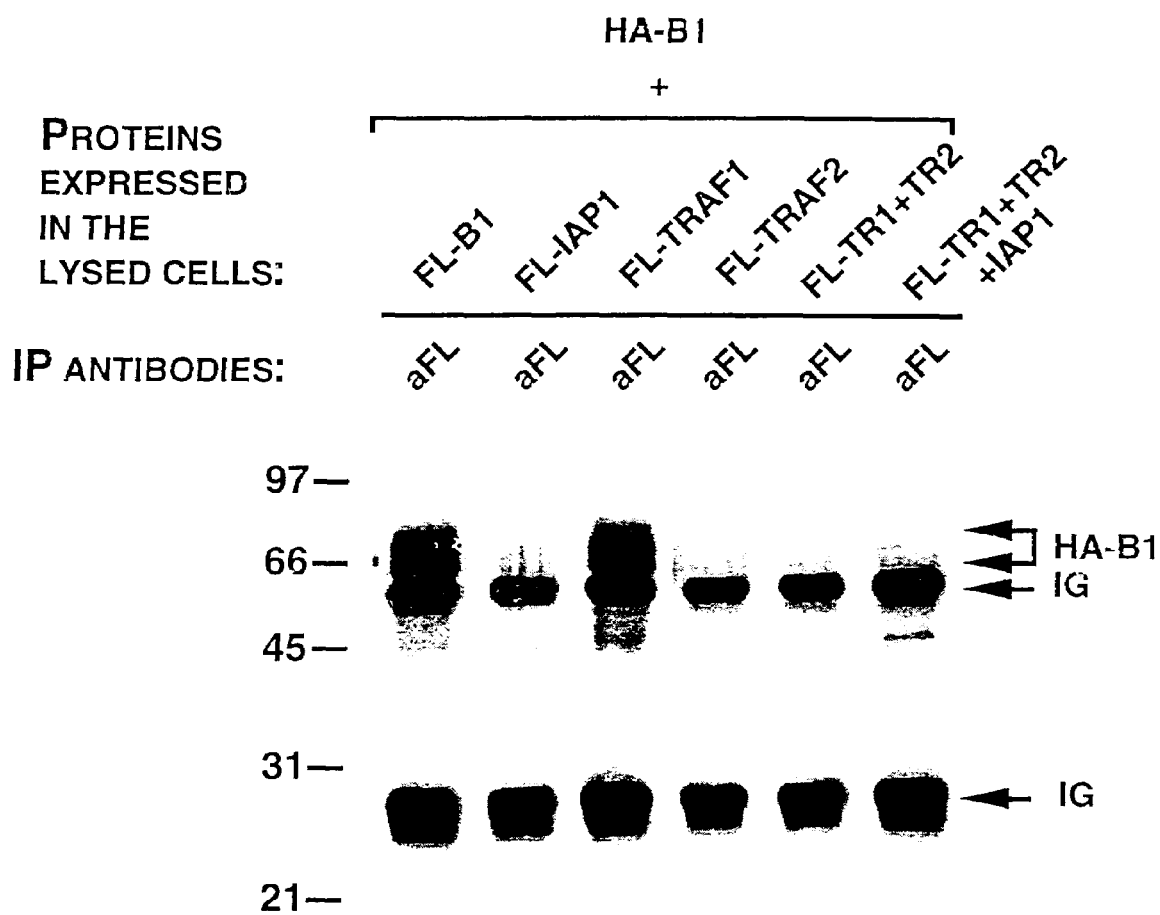
FIG. 8 shows that B1 self-associates and binds TRAF1 in vivo.

It is apparent from FIG. 8 that B1 is able to self-associate as well as to interact with TRAF-1. The level of interaction appears to be about the same as its self-association. No direct interaction with TRAF-2 or 1AP1 is observed.

EXAMPLE 5

B1 Binds to the E Subunit of V-ATPase

Two hybrid screens with CARD domain of B1 as a bait resulted in cloning the E subunit of V-ATPase (the review by Nelson et al., Experientia 52 (1996) pp. 1101-1110).

The E subunit of V-ATPase is labeled fluorescently and incubated with a sample of the CARD domain of B1 in the presence of various samples of a library of organic molecules or peptides. Following incubation, the B1-CARD motif is immunoprecipitated with specific antibodies and the amount of fluorescence associated with this precipitate is measured. Molecules found to interfere with precipitation of the fluorescently labeled E-protein are further examined as potential lead compound as drugs which affect cell viability or growth and/or inflammation via the function of the E-subunit of ATPase.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Adelman et al., (1983) DNA 2, 183.
2. Alnemri, E. S. et al. (1995) J. Biol. Chem. 270, 4312-4317.
3. Ausubel, F. M. et al. (1994) eds., Current Protocols in Molecular Biology.
4. Baeuerle, P. A., and Henkel, T. (1994) Annu Rev Immunol.
5. Bazan, J. F. (1993). Current Biology 3), 603-606.
6. Berberich, I., Shu, G. L., and Clark, E. A. (1994). J Immunol 153, 4357-66.
7. Beutler, B., and van Huffel, C. (1994). Science 264, 667-8.
8. Blank, V., Kourilsky, P., and Israel, A. (1992). Trends Biochem. Sci 17, 135-40.
9. Boldin, M. P. et al. (1995a) J. Biol. Chem. 270, 337-341.
10. Boldin, M. P., Varfolomeev, E. E., Pancer, Z., Mett, I. L., Camonis, J. H., and Wallach, D. (1995b). J. Biol. Chem. 270, 7795-7798.
11. Boldin, M. P. et al. (1996) Cell 85, 803-815.
12. Cao, Z. et al. (1996a) Nature 383, 443-446.
13. Cao, Z. et al. (1996b) Science 271, 1128-1131.
14. Chen, C. J. et al. (1992) Ann. N.Y. Acad. Sci. 660:271-273.
15. Cheng, G., Cleary, A. M., Ye, Z-s., Hong, D. I., Lederman, S. and Baltimore, D. (1995) Science 267:1494-1498).
16. Cheng, G. and Baltimore, D. (1996) Genes Dev. 10, 963-973.
17. Chinnaiyan, A. M., O'Rourke, K., Tewari, M., and Dixit, V. M. (1995) Cell 81, 505-512.
18. Chinnaiyan, A. M. et al. (1996) J. Biol. Chem.-271, 4573-4576.
19. Creighton, T. E., Proteins: Structure and Molecular Properties, W.H. Freeman & Co., San Francisco, Calif. 1983.
20. Croston, G. E., Cao, Z., and Goeddel, D. V. (1995). J Biol Chem 270, 16514-7.
21. DiDonato, J. A., Mercurio, F., and Karin, M. (1995). Mol Cell Biol 15, 1302-11.
22. Duan, H. and Dixit, V. M. (1997) Nature 385, 86-89.
23. Durfee, T. et al. (1993) Genes Dev. 7:555-569.
24. Field, J. et al. (1988) Mol. Cell Biol. 8:2159-2165.
25. Geysen, H. M. (1985) Immunol. Today 6, 364-369.

26. Geysen, H. M. et al. (1987) J. Immunol. Meth. 102, 259-274.
27. Gilmore, T. D., and Morin, P. J. (1993). Trends Genet 9, 427-33.
28. Gossen, M. and Bujard, M. (1992) PNAS 89:5547-5551.
29. Grell, M., Douni, E., Wajant, H., Lohden, M., Clauss, M., Baxeiner, B., Georgopoulos, S., Lesslauer, W., Kollias, G., Pfizenmaier, K., and Scheurich, P. (1995). Cell 83, 793-802.
30. Grilli, M., Chiu, J. J., and Lenardo, M. J. (1993). Int RevCytol.
31. Hanks, S. K., Quinn, A. M., and Hunter, T. (1988). Science 241, 42-52.
32. Hofmann K. et al., (1997) TIBS May 22, 1997, p. 155-156.
33. Howard, A. D. et al. (1991) J. Immunol. 147, 2964-2969.
34. Hsu, H., Shu, H.-B., Pan, M.-G., and Goeddel, D. V. (1996). Cell 84, 299-308.
35. Hsu, H., Xiong, J., and Goeddel, D. V. (1995). Cell 81, 495-504.
36. Kaufmann, S. H. (1989) Cancer Res. 49, 5870-5878.
37. Kaufmann, S. H. (1993) Cancer Res. 53, 3976-3985.
38. Lalmanach-Girard, A. C., Chiles, T. C., Parker, D. C., and Rothstein, T. L. (1993). J Exp Med 177, 1215-1219.
39. Lazebnik, Y. A. et al. (1994) Nature 371, 346-347.
40. Malinin, N. L. et al., (1997) Nature 385, 540-544.
41. Mashima, T. et al. (1995) Biochem. Biophys. Res. Commun. 209, 907-915.
42. McDonald, P. P., Cassatella, M. A., Bald, A., Maggi, E., Romagnani, S., Gruss, H. J., and Pizzolo, G. (1995). Eur J Immunol 25, 2870-6.
43. Messing et al., Third Cleveland Symposium on Macromolecules and Recombinant DNA, Ed. A. Walton, Elsevier, Amsterdam (1981)
44. Milligan, C. E. et al. (1995) Neuron 15, 385-393.
45. Mosialos, G., Birkenbach, M., Yalamanchili, R., VanArsdale, T., Ware, C., and Kieff, E. (1995). Cell 80, 389-399.
46. Muranishi, S. et al. (1991) Pharm. Research 8, 649.
47. Nagata, S. and Golstein, P. (1995) Science 267, 1449-1456.
48. Rensing-Ehl, A., Hess, S., Ziegler-Heitbrock, H. W. L., Riethmüller, G., and Engelmann, H. (1995). J. Inlamm. 45, 161-174.
49. Rothe, M., Pan, M.-G., Henzel, W. J., Ayres, T. M., and Goeddel, D. V. (1995b). Cell 83, 1243-1252.
50. Rothe, M., Sarma, V., Dixit, V. M., and Goeddel, D. V. (1995a). Science 269, 1424-1427.
51. Rothe, M., Wong, S. C., Henzel, W. J., and Goeddel, D. V. (1994). Cell 78, 681-692.
52. Rothe, M. et al. (1996) Proc. Natl. Acad. Sci. U.S.A. 93, 8241-8246.
53. Ruzicka et al., (1993) Science 260, 487.
54. Sambrook et al. (1989) Molecular cloning: a laboratory manual, Cold Spring Harbor Laboratory Press, Cold Spring Harbor, N.Y.
55. Sano et al., (1992) Science 258, 120.
56. Sano et al., (1991) Biotechniques 9, 1378.
57. Schreiber, E., Matthias, P., Muller, M. M. and Schaffner, W. (1989), Nuc. Acids Res. 17:6419.
58. Schulz et al., G. E., Principles of Protein Structure, Springer-Verlag, New York, N.Y. 1798.
59. Sleath, P. R. et al. (1990) J. Biol. Chem. 265, 14526-14528.
60. Smith, C. A., Farrah, T., and Goodwin, R. G. (1994). Cell 76, 959-962.
61. Stanger, B. Z. et al. (1995) Cell 81, 513-523.
62. Thornberry, N. A. et al. (1992) Nature 356, 768-774.
63. Thornberry, N. A. et al. (1994) Biochemistry 33, 3934-3940.
64. Uren, A. G. et al. (1996) Proc. Natl. Acad. Sci USA 93, 4974-4978.
65. Vandenabeele, P., Declercq, W., Beyaert, R., and Fiers, W. (1995). Trends Cell Biol. 5, 392-400.
66. Varfolomeev, E. E., Boldin, M. P., Goncharov, T. M., and Wallach, D. (1996) J. Exp. Med. in press.
67. Vassalli, P. (1992) Ann. Rev. Immunol. 10, 411-452.
68. Veira et al., (1987) Meth. Enzymol. 153, 3.
69. Wallach, D. (1996) Eur. Cytokine Net. 7, 713-724.
70. Wallach, D. (1997) Trends Biochem. Sci. 22, 107-109.
71. Wang, L. et al. (1994) Cell 78, 739-750.
72. Wilks, A. F. et al. (1989) Proc. Natl. Acad. Sci. USA, 86:1603-1607.
73. Yang, E. and Korsmeyer, J. (1996) Blood 88(2), 386-401.
74. Zaccharia, S. et al. (1991) Eur. J. Pharmacol. 203, 353-357.
75. Zhao, J. J. and Pick, L. (1993) Nature 365: 448-451.

---

The invention claimed is:

1. An isolated DNA sequence comprising a sequence encoding a polypeptide which enhances the level of cell death induced by FAS-R, p55 TNF-R or RIP, said polypeptide comprising:

(a) a sequence comprising SEQ ID NO:1;

(b) a sequence comprising an analog of (a) which comprises amino acid residues 1-454, 244-540 or 315-540 of SEQ ID NO:1 and has no more than ten changes in the amino acid sequence of (a), each said change being a substitution, deletion or insertion of a single amino acid outside said amino acid residues 1-454, 244-540 or 315-540 of SEQ ID NO:1, which analog enhances the level of cell death induced by FAS-R, p55 TNF-R or RIP; or (c) a fragment of the sequence of SEQ ID NO:1, which fragment comprises amino acid residues 1-454, 244-540 or 315-540 of SEQ ID NO:1 and enhances the level of cell death induced by FAS-R, p55 TNF-R or RIP.

2. A DNA sequence in accordance with claim 1 comprising a sequence encoding a polypeptide of a sequence comprising SEQ ID NO:1.

3. A DNA sequence in accordance with claim 1, comprising a sequence encoding a polypeptide consisting of the sequence of (b).

4. A DNA sequence in accordance with claim 1, comprising a sequence encoding a polypeptide consisting of the sequence of (c).

5. A DNA sequence in accordance with claim 1, comprising SEQ ID ID NO:2.

6. An isolated DNA sequence in accordance with claim 1 wherein the entire DNA sequence is a coding sequence encoding said polypeptide.

7. A vector comprising a DNA sequence according to claim 1.

8. A vector according to claim 7 capable of being expressed in a eukaryotic host cell.

9. A vector according to claim 7 capable of being expressed in a prokaryotic host cell.

10. An isolated transformed eukaryotic or prokaryotic host cell containing a vector according to claim 7.

11. A composition comprising
a pharmaceutically acceptable excipient and a recombinant animal virus vector comprising a DNA sequence according to claim 1.

12. A method for producing a polypeptide which enhances the level of cell death induced by FAS-R, p55 TNF-R or RIP, which comprises growing a transformed host cell according to claim 11 under conditions suitable for the expression of an expression product, effecting post-translational modification of said expression product, as necessary, for obtaining said polypeptide, and isolating said expressed polypeptide.

* * * * *